(12) United States Patent
Han et al.

(10) Patent No.: US 12,144,866 B2
(45) Date of Patent: Nov. 19, 2024

(54) TRANSFERRIN BINDING ANTIBODIES AND USE THEREOF

(71) Applicant: LINNO PHARMACEUTICALS INC., Shanghai (CN)

(72) Inventors: Zhaozhong Han, Shanghai (CN); Hongya Pan, Shanghai (CN); Mengfan Peng, Shanghai (CN)

(73) Assignee: LINNO PHARMACEUTICALS INC., Shanghai (CN)

( * ) Notice: Subject to any disclaimer, the term of this patent is extended or adjusted under 35 U.S.C. 154(b) by 0 days.

(21) Appl. No.: 18/327,091

(22) Filed: Jun. 1, 2023

(65) Prior Publication Data

US 2024/0131177 A1 Apr. 25, 2024
US 2024/0226315 A9 Jul. 11, 2024

Related U.S. Application Data

(63) Continuation of application No. PCT/CN2021/135059, filed on Dec. 2, 2021.

(51) Int. Cl.
*A61K 47/68* (2017.01)
*C07K 16/18* (2006.01)

(52) U.S. Cl.
CPC ...... *A61K 47/6843* (2017.08); *A61K 47/6811* (2017.08); *A61K 47/6829* (2017.08); *C07K 16/18* (2013.01); *C07K 2317/569* (2013.01)

(58) Field of Classification Search
None
See application file for complete search history.

(56) References Cited

U.S. PATENT DOCUMENTS

2015/0210762 A1 7/2015 Farrington et al.
2016/0200830 A1 7/2016 Zhang et al.

FOREIGN PATENT DOCUMENTS

| CN | 105555310 | 5/2016 |
| CN | 111526887 | 8/2020 |
| CN | 113474369 | 10/2021 |

OTHER PUBLICATIONS

International Search Report issued Sep. 6, 2022, in Chinese Patent Application No. PCT/CN2021/135059 (References 1, 2, 15, 24 and 25 are cited therein).
Seung-Uon Shin, et al., "Transferrin-Antibody Fusion Proteins are Effective in Brain Targeting", *Pro. Natl. Acad. Sci.*, No. 7, vol. 92, pp. 2820-2824 (Mar. 1995).
Hiroyuki Sonoda, et al., "A Blood-Brain-Barrier-Penetrating Anti-human Transferrin Receptor Antibody Fusion Protein for Neuronopathic Mucopolysaccharides II," *Molecular Therapy*, vol. 26, No. 5, pp. 1366-1374, (May 2018).
Yang Gao, et al., "Single Domain Antibody-Based Vectors in the Delivery of Biologics Across the Blood-Brain Barrier: A Review," *Engineering Research Center of Cell and Therapeutic Antibody*, Ministry of Education, School of Pharamcy, Shanghai, China, Nov. 5, 2020; https://doi.org/10.1007/s13346-020-00873-7.

*Primary Examiner* — Ruixiang Li
(74) *Attorney, Agent, or Firm* — Oblon, McClelland, Maier & Neustadt, L.L.P.

(57) ABSTRACT

The present disclosure provides a method to translocate a molecule across cellular membrane by using a transferrin-binding protein. The transferrin-binding protein is capable of specifically binding to transferrin and not disturbing the interaction between transferrin and transferrin receptor.

13 Claims, 29 Drawing Sheets

Specification includes a Sequence Listing.

FIG. 3C-2

TRANSFERRIN BINDING ANTIBODIES AND USE THEREOF

In accordance with 37 CFR § 1.52(e)(5) and with 37 CFR § 1.831, the specification makes reference to a Sequence Listing submitted electronically as a .xml file named "547144US_ST26". The .xml file was generated on May 26, 2023 and is 143,059 bytes in size. The entire contents of the Sequence Listing are hereby incorporated by reference.

BACKGROUND OF THE INVENTION

Transmembrane drug delivery systems could be applied for blood-brain barrier (BBB)-crossing drug delivery, oral drug delivery, intracellular drug delivery and the like. Currently, among the non-invasive blood-brain barrier drug delivery technologies such as receptor-mediated BBB-crossing drug delivery, transferrin receptor (TfR) has been the most widely studied target protein. Those TfR-targeting vehicles include antibody clones known as OX26 and 8D3 in a format as Fabs, scFv, or dual-variable-domain immunoglobulin, a peptide known as GYR22, and an engineered Fc region of human IgG with TfR-binding properties. Although most of such approaches are still at a preclinical stage, some studies have shown promising results in clinical trials, even with several limitations.

TfR antibody affinity and valency can alter intracellular trafficking of the TfR and delivered therapeutic entities; high-affinity bivalent TfR antibodies were shown to divert the antibody-TfR complex into lysosomes, resulting in degradation and reduced levels of TfR. Therefore, TfR antibodies used for transmembrane drug delivery need to be optimal regarding affinity to TfR and/or monovalent to achieve higher efficiencies of transcytosis into the brain. The efficiency of TfR-targeting delivery technologies may vary upon biological or biochemical features of the to-be-delivered entities, anti-TfR antibodies may also cause acute clinical signs and a decrease of circulate reticulocyte count. Ubiquitous expression of TfR throughout the body, suggests that a TfR-targeting strategy will probably result in enhanced uptake of a TfR-targeted drug into peripheral compartments, such as the bone marrow, liver and spleen.

With a few exceptions, oral administration is currently an option only for small drug molecules that show acceptable intestinal absorption. As a rapidly expanding class of drugs, biologics are presently predominantly given by injection. Significant research efforts over decades have explored technologies to enable oral delivery of biologics, but progress has been relatively less impressive. Drug delivery strategies in this area mostly utilize absorption or permeation enhancers such as SNAC or focus on biologics with a relatively smaller mass, such as glucagon-like peptide 1 (GLP-1) analogues. However, safety concerns, including those related to many surfactants used for formulation, have hindered the clinical translation of these approaches. The key challenge in the field of oral delivery of macromolecular biologics concerns the difficulty in overcoming the formidable intestinal epithelial barrier, rather than additional barriers such as the stomach acid and mucosal enzymes, which can be addressed via relatively established technologies. A key requirement for technologies enabling therapeutically-relevant oral delivery of biologics is safety. Rather than disrupting and increasing the permeability of the intestinal epithelium non-selectively (i.e., an effect that a classical permeation enhancer would display), it is desirable to engineer delivery systems that selectively permeate the intestinal mucosa.

SUMMARY OF THE INVENTION

The present disclosure provides a method to translocate a molecule across cellular membrane by using a transferrin-binding protein. The transferrin-binding protein is capable of specifically binding to transferrin and not disturbing the interaction between transferrin and transferrin receptor.

In one aspect, the present disclosure provides a method to translocate a molecule across cellular membrane by using a transferrin-binding protein.

In some embodiments, the transferrin-binding protein comprises a transferrin binding antibody or its fragment.

In some embodiments, the method is used for drug delivery across cellular membrane of a polarized and/or unpolarized cell.

In some embodiments, the polarized and/or unpolarized cell expresses transferrin receptor on its cellular membrane.

In some embodiments, the drug delivery across cellular membrane of an unpolarized cell comprises intracellular delivery of drug, and/or recycling of an endocytosed drug back to circulation.

In some embodiments, the drug delivery across cellular membrane of a polarized cell comprises crossing blood brain barrier (BBB) of central nervous system (CNS)-targeted systemically dosed drug, crossing intestinal epithelium of orally administered drug, and/or penetration of drug through multiple layers of cells in a solid tissue.

In some embodiments, the drug comprises a therapeutic or diagnostic substance.

In some embodiments, the drug comprises a small molecular compound, a synthetic peptide, a recombinant protein, an antibody or antibody fragment, an enzyme, a piece of nucleotide acid sequence, a liposome, a lipid nanoparticle, a drug vehicle, a synthetic nucleotide sequence, a modified virus and/or a gene-therapy vector.

In some embodiments, the drug is associated to the transferrin-binding protein through chemical conjugation or genetic fusion.

In another aspect, the present disclosure provides a transferrin-binding protein, which being capable of extending half-life in circulation of its associated entities.

In some embodiments, the transferrin-binding protein enables a drug comprising the transferrin-binding protein to cross blood-brain barrier (BBB).

In some embodiments, the transferrin-binding protein is used for oral delivery of a drug.

In some embodiments, the transferrin-binding protein enables intracellular delivery of its associated entities to transferrin receptor-expressing cells.

In some embodiments, the transferrin-binding protein is capable of specifically binding to transferrin and not disturbing the interaction between transferrin and transferrin receptor 1.

In some embodiments, the transferrin is a human transferrin.

In some embodiments, the transferrin-binding protein possesses a higher affinity to iron-containing holo-transferrin than that to iron-free apo-transferrin.

In some embodiments, the transferrin-binding protein comprises monoclonal antibody, single chain antibody fragment, single domain antibody fragment, engineered protein, or a peptide.

In some embodiments, the antibody or antibody fragment comprises animal-derived sequence, humanized sequence, fully human sequence, a chimeric sequence, or a synthetic sequence.

In some embodiments, the antibody or antibody fragment is a single domain antibody fragment VHH.

In some embodiments, the transferrin-binding protein comprises a CDR3, the CDR3 comprises an amino acid sequence as set forth in any one of SEQ ID NOs: 45-69.

In some embodiments, the transferrin-binding protein comprises a CDR1, a CDR2 and a CDR3, and the CDR3 comprises an amino acid sequence as set forth in any one of SEQ ID NOs: 45-69.

In some embodiments, the transferrin-binding protein comprises a heavy chain variable region VH, the heavy chain variable region VH comprises an amino acid sequence as set forth in any one of SEQ ID Nos: 70-104.

In another aspect, the present disclosure provides a polypeptide comprises the transferrin-binding protein, and a therapeutic entity.

In some embodiments, the therapeutic entity comprises an engineered cytotoxic *Pseudomonas* exotoxin A (PE38).

In some embodiments, the therapeutic entity is a glucagon-like peptide-1 (GLP-1) or its variant.

In some embodiments, the therapeutic entity and said antigen-binding protein are directly or indirectly linked.

In some embodiments, the therapeutic entity and the transferrin-binding protein are linked through a linker.

In another aspect, the present disclosure provides one or more isolated nucleic acid molecules, encoding the transferrin-binding protein, or the polypeptide as set forth in any one of SEQ ID NOs: 70-106.

In another aspect, the present disclosure provides a vector, comprising the nucleic acid molecules encoding a polypeptide as set forth in any one of SEQ ID NOs: 70-106.

In another aspect, the present disclosure provides a cell, comprising the nucleic acid molecule or the vector expressing a polypeptide as set forth in any one of SEQ ID NOs: 70-106.

In another aspect, the present disclosure provides a method of preparing the transferrin-binding protein, or the polypeptide, comprising culturing the cell under conditions that allow the transferrin-binding protein or the polypeptide to be expressed.

In another aspect, the present disclosure provides a pharmaceutical composition, comprising the transferrin-binding protein or the polypeptide.

In another aspect, the present disclosure provides a method for extending half-life in circulation of a therapeutic entity, wherein the therapeutic entity is linked with the transferrin-binding protein directly or indirectly.

In another aspect, the present disclosure provides a method for delivering a therapeutic drug or diagnostic agent to transferrin receptor-expressing cells or organs, comprising using a transferrin-binding entity.

In another aspect, the present disclosure provides a method for delivering a targeted drug to cross blood-brain barrier, intestinal epithelium and/or cell membranes that express transferrin receptor, comprising using a transferrin-binding entity.

In another aspect, the present disclosure provides a method for oral delivery of a therapeutic or diagnostic entity, the therapeutic or diagnostic entity is linked with the antigen binding protein directly or indirectly.

In another aspect, the present disclosure provides a method for intracellular delivery of a therapeutic entity, the therapeutic entity is linked with the antigen binding protein directly or indirectly.

The present disclosure provides a technical solution that utilize Tf instead of TfR for targeting which the drug delivery system is based on. The present disclosure obtains multiple potential advantages regarding specificity, safety, efficiency and half-life in circulation.

Additional aspects and advantages of the present disclosure will become readily apparent to those skilled in this art from the following detailed description, wherein only illustrative embodiments of the present disclosure are shown and described. As to be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

The novel features of the invention are set forth with particularity in the appended claims. A better understanding of the features and advantages of the present invention will be obtained by reference to the following detailed descriptions that set forth illustrative embodiments, in which the principles of the invention are employed, and the accompanying drawings (also "figure" and "FIG." herein), of which:

FIGS. 3A, 3B, 3C-1, and 3C-2 illustrates transferrin-mediated binding of the selected transferrin binding protein-OVA-His proteins to the transferrin receptor-expressing cells.

FIG. 9A-9B illustrates the intracellular delivery of the transferrin binding protein—PE38 on different cells.

DETAILED DESCRIPTION

Figure 1:
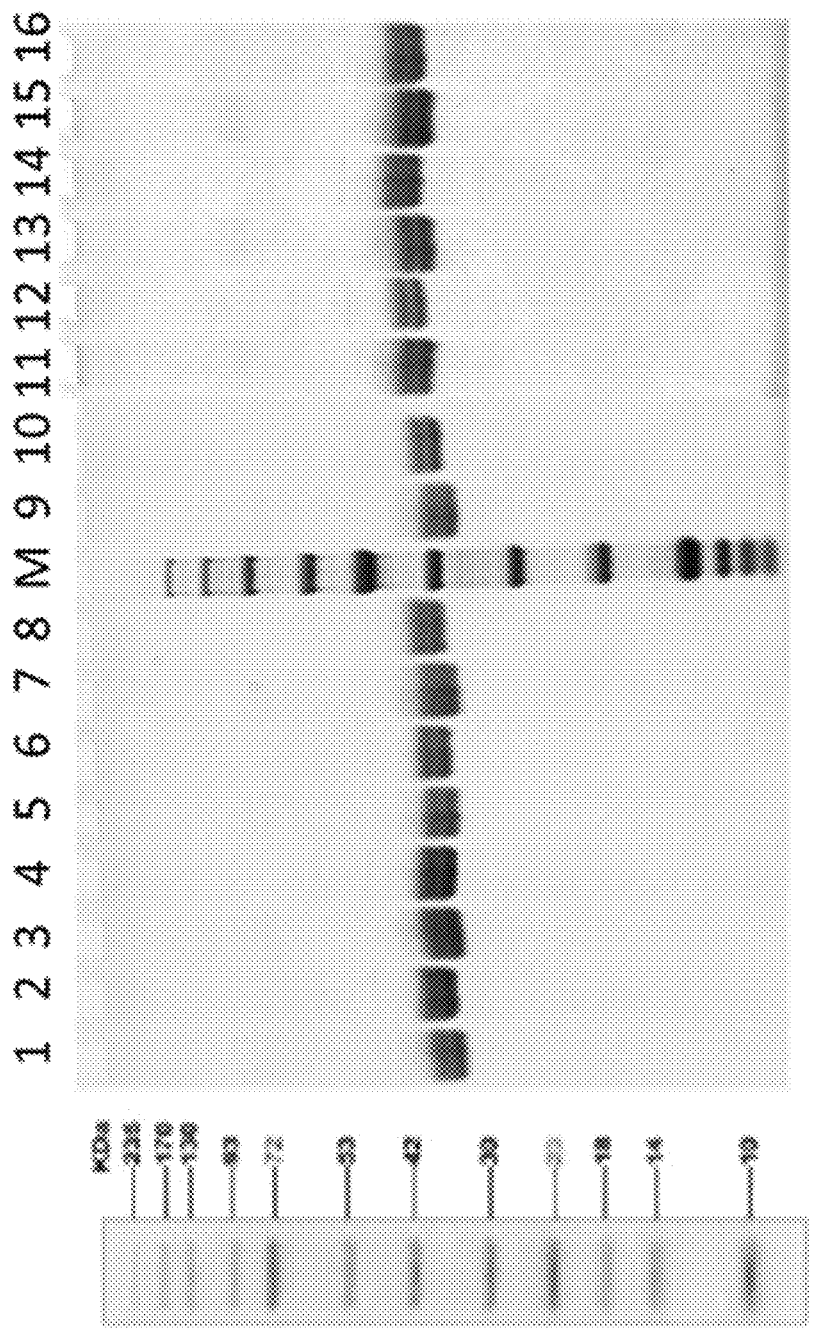
FIG. 1 illustrates representative SDS-PAGE of the transferrin binding protein-OVA-his proteins expressed in HEK293 cells.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

In the present application, the term "cellular membrane" generally refers to an interface that separates the different media and components inside and outside the cell in the cell structure. Plasma membranes are generally believed to be represented as the basic unit of phospholipid bilayer molecules, that is, phospholipid bilayers, on which various types of membrane proteins, as well as sugars and glycolipids bound to membrane proteins, are inlaid. Through the pores and certain properties of transmembrane proteins, it can achieve selective and controllable material transport. For example, the cellular membrane may belong to a polarized. For example, the cellular membrane may belong to a unpolarized cell.

In the present application, the term "polarized cell" generally refers to a cell with stable asymmetry in structure and function, such as a cell at resting potential, ready to transmit nerve impulse signals. The term "unpolarized cell" generally refers to a cell with a change in resting potential and transmits nerve impulse signals. For example, the polarized cell and/or unpolarized cell may belong to the blood brain barrier of central nervous system. For example, the polarized cell and/or unpolarized cell may belong to the intestinal epithelium. For example, the polarized cell and/or unpolarized cell may belong to a solid tissue.

In the present application, the term "transferrin-binding protein" generally refers to a protein including an antigen-binding portion, and optionally it is allowed the antigen-binding portion to adopt a scaffold or skeleton portion in a conformation that promotes the binding of the antigen binding protein to the antigen. For example, the antigen binding protein may include, but not limit to, an antibody, an antigen binding fragment (Fab, Fab', F(ab)2, a Fv fragment, F(ab')2, scFv, di-scFv and/or dAb), an immunoconjugate, a multiple specific antibody (e.g., a bispecific antibody), an antibody fragment, an antibody derivative, an antibody analogue or a fusion protein, as long as they show the desired antigen binding activity. For example, the antigen binding protein may be capable of specifically binding to transferrin. For example, the antigen binding protein may not disturb the interaction between transferrin and transferrin receptor 1. For example, the antigen binding protein may not affect Tf/TfR1 binding. For example, the antigen binding protein may maintain the normal physiological function of iron transport.

In the present application, the term "transferrin" generally refers to a glycoprotein which can bind to and transport multivalent ions. For example, the transferrin may be a single-chain glycoprotein. For example, the transferrin may have a molecular weight of about 77,000 D. For example, the transferrin may have a polysaccharide. For example, the transferrin may have two ion binding sites. For example, the ion binding sites may have different affinity with iron ions. For example, the multivalent ion may be an iron ion, a chromium ion, a manganese ion, a cadmium ion or a nickel ion thereof. For example, each molecule of transferrin may bind two trivalent iron atoms. For example, transferrin could be iron-containing holo-transferrin, or iron-free apo-transferrin. For example, the transferrin may be a mice transferrin. For example, the amino sequence of mice transferrin may be as set forth in GenBank: EDL21066.1, AAL34533.1, or AAL34533.1. For example, the transferrin may be a human transferrin. For example, the amino sequence of human transferrin may be as set forth in GenBank: AAH59367.1, AAH59367.1, or AAB22049.1.

In the present application, the term "transferrin receptor" generally refers to a carrier protein of transferrin. For example, the transferrin may be a transmembrane glycoprotein. For example, the transferrin receptor may mediate endocytosis of transferrin associated to two iron ions. For example, the transferrin receptor may maintain iron homeostasis in cells. For example, the transferrin receptor may be transferrin receptor 1 (TfR1) or transferrin receptor 2 (TfR2). For example, TfR1 and TfR2 may show homologies around 45-66% in the extracellular domain but present with different expression patterns in the body. For example, the TfR1 may have higher affinity to transferrin than that of TfR2. For example, TfR2 may have a 25-fold lower affinity with transferrin compared to that of TfR1. For example, the TfR2 may mainly express in tissues involved in regulating iron metabolism, such as the liver and small intestines, while the TfR1 is generally found on the surface of most body cells. The term "transferrin receptor 1" generally refers to a 97-kDa type2 membrane protein expressed as a homodimer in the cell membrane. TfR1-mediated transferrin internalization is classically described as the canonical iron import pathway. For example, the transferrin receptor may be a mouse transferrin receptor. For example, the amino sequence of mouse transferrin receptor may be as set forth in GenBank: AAH54522.1, CAA40624.1, or NP_001344227.1. For example, the transferrin receptor may be a human transferrin receptor. For example, the amino sequence of human transferrin receptor may be as set forth in GenBank: AAA61153.1, AAF04564.1, or AAB19499.1.

In the present application, the term "half-life" generally refers to the time required to reduce the 50% levels in the serum concentration of an amino acid sequence, compound, or polypeptide due to degradation of the sequence or compound by natural mechanisms and/or clearance or sequestration of the sequence or compound in the body. The half-life can be evaluated by methods known to those skilled in the art. The in vivo half-life of the amino acid sequence, compound or polypeptide of the present invention can be determined in any known manner, such as by pharmacokinetic analysis. Suitable techniques are obvious to the person skilled in the art, for example, as described in paragraph o) on page 57 of WO 08/020079. Also as mentioned in paragraph o) on page 57 of WO 08/020079, parameters such as t½-α, t½-β and area under the curve (AUC) can be used to express the half-life. In this respect, it should be noted that the term "half-life" in the present application specifically refers to t½-β or terminal half-life (where t½-α and/or AUC can be ignored). For example, refer to the following experimental parts and standard manuals, such as Kenneth, A, etc.: Chemical Stability of Pharmaceuticals: A Handbook for Pharmacists and Peters, etc., Pharmacokinete analysis: A Practical Approach (pharmacokinetics) Analysis: Practice Method) (1996). Also refer to "Pharmacokinetics", M Gibaldi & #x26; DPerron, Published by Marcel Dekker, 2nd Edition, (1982).

In the present application, the term "fusion protein" generally refers to a chimeric protein including the amino acid sequence of two or more different proteins, although the different proteins are not combined in their natural state, their respective amino and carboxyl ends are bound via peptide bonds to form a continuous polypeptide. It should be understood that the two or more different proteins may be directly bound via a peptide linker or spacer. For example, the fusion protein may include a prophylactic or therapeutic drug fused to a heterologous protein, polypeptide, or peptide. Wherein, the heterologous protein, polypeptide or peptide may or may not be different types or therapeutic drugs. For example, the fusion protein may comprise two different proteins, polypeptides or peptides with immunomodulatory activity. For example, the fusion protein may retain or improve the activity compared to the activity of the original polypeptide or protein. Typically, the fusion protein can be produced by in vitro recombinant techniques well known in the art. For example, the fusion protein may comprise the antigen binding protein. For example, the fusion protein may comprise biologic molecules.

In the present application, the term "blood-brain barrier (BBB)", generally refers to the physiological barrier between the peripheral circulation and the brain and spinal cord. It is formed by the tight junctions in the plasma membrane of brain capillary endothelial cells and constitutes a tight barrier that restricts the transport of molecules to the brain, even very small molecules such as urea (60 Daltons). For example, the brain capillary endothelial cells may have weaker pinocytosis. For example, the blood-brain barrier may include the BBB in the brain, the blood-spinal cord barrier in the spinal cord, and the blood-retinal barrier in the retina. For example, the BBB may also include the blood-CSF barrier (choroid plexus), where the barrier is composed of ependymal cells instead of capillary endothelial cells.

In the present application, the term "oral delivery of a drug" generally refers to the drug is absorbed into the blood by the gastrointestinal tract after oral administration, and reaches the local or systemic tissues through blood circulation to achieve the purpose of curing or preventing diseases. For example, the drug may comprise transferrin-binding protein. For example, the drug may comprise biologic molecules.

In the present application, the term "associated entity" generally refers to any monomeric or multimeric protein, protein fragment, nucleotide sequence, small molecular compound, a delivery vehicle, or a modified transgene vector that was specifically linked to an antigen binding protein. The associated entity includes but is not limited to antibodies and binding parts thereof, such as immunologically functional fragments. For example, the antigen binding protein may be transferrin-binding protein. In the present application, the term "therapeutic entity" generally refers to any monomeric or multimeric protein or protein fragment that have the function of curing or preventing diseases.

In the present application, the term "a heavy chain variable region (VH)" generally refers to the region of the immunoglobulin heavy chain structure that contains the heavy chain complementarity determining regions CDR1, CDR2, CDR3 and framework regions FR1, FR2, FR3, FR4. The variable region of the heavy chain may contain a binding domain that interacts with an antigen. For example, the heavy chain variable region of the present application may include a region that specifically binds to transferrin. For example, the heavy chain variable region of the present application may include the VHH of a single domain antibody.

In the present application, the terms "CDR" and "CDRs" generally refer to complementarity determining regions (CDR), where the three constitute the binding properties of the light chain variable region (LCDR1, LCDR2 and LCDR3) and the three constitute the heavy chain variable regions (HCDR1, HCDR2 and HCDR3). CDR contributes to the functional activity of the antibody molecule and is separated by an amino acid sequence containing a backbone or framework region. The precisely defined CDR boundaries and lengths are subject to different classification and numbering systems.

In the present application, the terms "polypeptide", "peptide" and "protein" are used interchangeably and refer to a polymer of amino acid residues. The term also applies to amino acid polymers in which one or more amino acids are chemical analogs or modified derivatives of the corresponding naturally occurring amino acids. For example, the polypeptide may comprise the antigen binding protein and other molecules. For example, the polypeptide may comprise a fusion antigen. For example, the antigen binding protein and the molecule may be directly or indirectly linked. For example, the antigen binding protein and the molecule may be linked via a linker. For example, the molecules may comprise a therapeutic molecule. For example, the molecule may comprise a PE38. For example, the molecule may comprise GLP-1 or an analogue.

In the present application, the terms "affinity" generally refers to the strength of the sum of non-covalent interactions between a single binding site of a molecule (e.g., polypeptide or antibody) and its binding partner (e.g., target or antigen). Unless otherwise specified, when used herein, "binding affinity" refers to the relationship between the members of a binding pair (e.g., in a polypeptide-polynucleotide-complex, or between a polypeptide and its target, or between an antibody and an antibody). The intrinsic binding affinity of 1:1 interaction between antigens. The affinity of a molecule X to its partner Y can usually be represented by the dissociation constant (Kd). Affinity can be measured by common methods known in the art, such as surface plasmon resonance, and also includes those methods reported herein. The higher affinity of molecule X to the binding partner Y can be seen in lower Kd and/or EC50 values.

In the present application, the term "isolated nucleic acid molecule" generally refers to a piece of nucleic acids encoding a specific amino acid sequence such as an antibody or antibody portion (for example, VH, VL, CDR3) that selectively binds transferrin, and means a nucleic acid sequence that encodes a fusion protein with the antibody or antibody portion therein.

In the present application, the term "vector" generally refers to a composition that includes an isolated nucleic acid and can be used to deliver the isolated nucleic acid to the inside of a cell. Many vectors are known in the art, including but not limited to linear polynucleotides, polynucleotides related to ionic or amphiphilic compounds, plasmids and viruses. Therefore, the term "vector" includes autonomously replicating plasmids or viruses. The term should also be interpreted to include non-plasmid and non-viral compounds that facilitate the transfer of nucleic acids into cells, such as, for example, polylysine compounds, liposomes, and the like. Examples of viral vectors include, but are not limited to adenoviral vectors, adeno-associated virus vectors, retroviral vectors, lentiviral vectors, and the like.

In the present application, the term "cell" generally refers to a single cell, cell line, or cell culture that can be or has been a recipient of a subject's plasmid or vector, which includes the nucleic acid molecule described in this application or the nucleic acid molecule described in this application. A cell can include the progeny of a single cell. Due to natural, accidental or deliberate mutations, the offspring may not necessarily be exactly the same as the original parent cell (in terms of the morphology of the total DNA complement or in the genome). The cells may include cells transfected in vitro with the vectors described in this application.

In the present application, the term "pharmaceutical composition" generally refers to a composition for preventing/treating a disease or condition. The pharmaceutical composition may comprise the antigen binding protein, the immunoconjugate, the isolated nucleic acid molecule, the vector and/or the cell, and optionally pharmaceutically acceptable adjuvant. In addition, the pharmaceutical composition may also include one or more (pharmaceutically effective) carriers and other suitable preparations. The acceptable ingredients of the composition are preferably non-toxic to the recipient at the dosage and concentration used. The pharmaceutical compositions of the present invention include, but are not limited to, liquid, frozen and lyophilized compositions.

Detailed Description of Invention

Transferrin-Binding Protein

In an aspect, the present application the present application provides a transferrin-binding protein which is capable of specifically binding to transferrin and not disturbing the interaction between transferrin and transferrin receptor 1.

For example, the transferrin-binding protein may be capable of extending half-life in circulation of its associated entities.

For example, the half-life may be evaluated by methods known to those skilled in the art. For example, the in vivo half-life of the amino acid sequence, compound or polypeptide of the present invention may be determined in any known manner, such as by pharmacokinetic analysis. Suitable techniques are obvious to the person skilled in the art, for example, as described in paragraph o) on page 57 of WO 08/020079. Also as mentioned in paragraph o) on page 57 of WO 08/020079, parameters such as $t^{1/2}$-α, $t^{1/2}$-β and area under the curve (AUC) can be used to express the half-life. In this respect, it should be noted that the term "half-life" in the present application specifically refers to $t^{1/2}$-β or terminal half-life (where $t^{1/2}$-α and/or AUC can be ignored). For example, refer to the following experimental parts and standard manuals, such as Kenneth, A, etc.: Chemical Stability of Pharmaceuticals: A Handbook for Pharmacists and Peters, etc.

For example, the associated entity may be any monomeric or multimeric protein, protein fragment, nucleotide sequence, small molecular compound, a delivery vehicle, or a modified transgene vector that was specifically linked to an antigen binding protein. For example, the associated entity may include but not limit to antibodies and binding parts thereof, such as immunologically functional fragments. For example, the antigen binding protein may be transferrin-binding protein.

For example, the transferrin-binding protein may enable a fusion protein comprising the transferrin-binding protein to cross blood-brain barrier (BBB).

For example, the BBB may be a physiological barrier between the peripheral circulation and the brain and spinal cord. For example, the BBB may comprise the tight junctions in the plasma membrane of brain capillary endothelial cells and constitutes a tight barrier that restricts the transport of molecules to the brain, even very small molecules such as urea (60 Daltons). For example, the brain capillary endothelial cells may have weaker pinocytosis. For example, the blood-brain barrier may comprise the BBB in the brain, the blood-spinal cord barrier in the spinal cord, and the blood-retinal barrier in the retina. For example, the BBB may also comprise the blood-CSF barrier (choroid plexus), where the barrier is composed of ependymal cells instead of capillary endothelial cells.

For example, the fusion protein may enter the brain tissue by crossing the BBB.

For example, the transferrin-binding protein may be used for oral delivery of a drug.

For example, the dosing form of the oral delivery of a drug may be a capsule, a granule, or a tablet.

For example, the transferrin-binding protein may enable intracellular delivery of its associated entities to transferrin receptor-expressing cells.

For example, the transferrin-binding protein may be capable of specifically binding to transferrin and not disturbing the interaction between transferrin and transferrin receptor 1.

For example, the transferrin may be a human transferrin.

For example, the transferrin may be iron-containing holo-transferrin.

For example, the iron-containing holo-transferrin may comprise the transferrin and $Fe^{3+}$.

For example, the transferrin may bind to $Fe^{3+}$.

For example, the transferrin may bind to two $Fe^{3+}$.

For example, the iron-containing holo-transferrin may bind to the transferrin receptor.

For example, the iron-containing holo-transferrin may bind to the transferrin receptor 1.

For example, the iron-containing holo-transferrin may be transported to the endosome by the transferrin receptor.

For example, the iron-containing holo-transferrin may be transported through endocytosis.

For example, the iron-containing holo-transferrin may be transported through transcytosis.

For example, the iron-containing holo-transferrin may separate from $Fe^{3+}$.

For example, the transferrin may be iron-free apo-transferrin.

For example, the iron-free apo-transferrin may be come from the iron-containing holo-transferrin separated from $Fe^{3+}$.

For example, the iron-free apo-transferrin may be capable of binding to $Fe^{3+}$.

For example, the transferrin-binding protein may posses a higher affinity to iron-containing holo-transferrin than that to iron-free apo-transferrin.

For example, the affinity may be measured by surface plasmon resonance-based assays.

For example, the affinity may be measured by enzyme-linked immunosorbent assays (ELISA).

For example, the affinity may be measured by competition assays (RIA).

For example, the affinity may be measured by flow cytometry (FACS).

For example, the affinity may be expressed as the binding equilibrium constant (KD).

For example, the affinity of transferrin-binding protein to iron-containing holo-transferrin may be 2-fold, 4-fold, 6-fold, 8-fold, 10-fold, 20-fold, 40-fold, 60-fold, 80-fold, 100-fold higher than that to iron-free apo-transferrin.

For example, the transferrin-binding protein may comprise monoclonal antibody.

For example, the transferrin-binding protein may comprise single chain antibody fragment.

For example, the transferrin-binding protein may comprise single domain antibody fragment.

For example, the transferrin-binding protein may comprise engineered protein.

For example, the transferrin-binding protein may comprise a peptide.

For example, the antibody or antibody fragment of the transferrin-binding protein may comprise animal-derived sequence.

For example, the antibody or antibody fragment of the transferrin-binding protein may comprise humanized sequence.

For example, the antibody or antibody fragment of the transferrin-binding protein may comprise fully human sequence.

For example, the antibody or antibody fragment of the transferrin-binding protein may comprise a chimeric sequence.

For example, the antibody or antibody fragment of the transferrin-binding protein may comprise a synthetic sequence.

For example, the antibody or antibody fragment of the transferrin-binding protein may be a single domain antibody fragment VHH.

In the present application, the transferrin-binding protein may include at least one CDR in a heavy chain variable region VH, wherein the VH includes an amino acid sequence as set forth in any of SEQ ID NOs: 70-104.

For example, the VH may include an amino acid sequence as set forth in any one of SEQ ID NOs: 70-104.

For example, the transferrin-binding protein may include the HCDR3 of the VH with an amino acid sequence as set forth in any one of SEQ ID NOs: 45-69.

For example, the transferrin-binding protein may include the HCDR2 of the VH with an amino acid sequence as set forth in any one of SEQ ID NOs: 22-44.

For example, the transferrin-binding protein may include the HCDR1 of the VH with an amino acid sequence as set forth in any one of SEQ ID NOs: 1-21.

For example, the transferrin-binding protein may comprise a HCDR1, a HCDR2, and a HCDR3, the HCDR1 may comprise an amino acid sequence as set forth in any one of SEQ ID NOs: 1-21, the HCDR2 may comprise an amino acid sequence as set forth in any one of SEQ ID NOs: 22-44, and the HCDR3 may comprise an amino acid sequence as set forth in any one of SEQ ID NOs: 45-69.

For example, the transferrin-binding protein may comprise a Fc region.

For example, the Fc region may comprise a human Fc region.

For example, the Fc region may comprise a human IgG Fc region.

For example, the Fc region may comprise a human IgG1 Fc region. For example, the Fc region may comprise a human IgG4 Fc region.

For example, the transferrin-binding protein may comprise an antibody or its antigen binding fragment. The antibody may be selected from the group consisting of monoclonal antibody, single strand antibody, chimeric antibody, polyspecific antibody, humanized antibody and fully human antibody. The antigen binding fragments is selected from the group consisting of Fab, Fab', F(ab)2, F(ab')2, sdAb, Fv, dAb and ScFv fragment.

For example, the transferrin-binding protein may be a VHH.

For example, the VHH may comprise a CDR3, and the CDR3 may comprise an amino acid sequence as set forth in any one of SEQ ID NOs:45-69.

For example, the VHH may comprise a CDR2, and the CDR2 may comprise an amino acid sequence as set forth in any one of SEQ ID NOs: 22-44.

For example, the VHH may comprise a CDR1, and the CDR1 may comprise an amino acid sequence as set forth in any one of SEQ ID NOs: 1-21.

For example, the VHH may comprise a CDR1, a CDR2, and a CDR3, the CDR1 may comprise an amino acid sequence as set forth in any one of SEQ ID NOs: 1-21, the CDR2 may comprise an amino acid sequence as set forth in any one of SEQ ID NOs: 22-44, and the CDR3 may comprise an amino acid sequence as set forth in any one of SEQ ID NOs:45-69.

For example, the VHH may comprise a CDR1, a CDR2, and a CDR3, the CDR1, the CDR2, and the CDR3 may comprise an amino acid sequence as set forth in SEQ ID NO: 1, SEQ ID NO: 22, and SEQ ID NO: 45, respectively; or the CDR1, the CDR2, and the CDR3 may comprise an amino acid sequence as set forth in SEQ ID NO: 1, SEQ ID NO: 22, and SEQ ID NO: 63, respectively; or the CDR1, the CDR2, and the CDR3 may comprise an amino acid sequence as set forth in SEQ ID NO: 2, SEQ ID NO: 23, and SEQ ID NO: 46, respectively; or the CDR1, the CDR2, and the CDR3 may comprise an amino acid sequence as set forth in SEQ ID NO: 2, SEQ ID NO: 23, and SEQ ID NO: 58, respectively; or the CDR1, the CDR2, and the CDR3 may comprise an amino acid sequence as set forth in SEQ ID NO: 2, SEQ ID NO: 40, and SEQ ID NO: 58, respectively; or the CDR1, the CDR2, and the CDR3 may comprise an amino acid sequence as set forth in SEQ ID NO: 2, SEQ ID NO: 41, and SEQ ID NO: 58, respectively; or the CDR1, the CDR2, and the CDR3 may comprise an amino acid sequence as set forth in SEQ ID NO: 2, SEQ ID NO: 23, and SEQ ID NO: 66, respectively; or the CDR1, the CDR2, and the CDR3 may comprise an amino acid sequence as set forth in SEQ ID NO: 3, SEQ ID NO: 24, and SEQ ID NO: 47, respectively; or the CDR1, the CDR2, and the CDR3 may comprise an amino acid sequence as set forth in SEQ ID NO: 4, SEQ ID NO: 25, and SEQ ID NO: 48, respectively; or the CDR1, the CDR2, and the CDR3 may comprise an amino acid sequence as set forth in SEQ ID NO: 5, SEQ ID NO: 26, and SEQ ID NO: 49, respectively; or the CDR1, the CDR2, and the CDR3 may comprise an amino acid sequence as set forth in SEQ ID NO: 6, SEQ ID NO: 27, and SEQ ID NO: 50, respectively; or the CDR1, the CDR2, and the CDR3 may comprise an amino acid sequence as set forth in SEQ ID NO: 6, SEQ ID NO: 27, and SEQ ID NO: 59, respectively; or the CDR1, the CDR2, and the CDR3 may comprise an amino acid sequence as set forth in SEQ ID NO: 7, SEQ ID NO: 28, and SEQ ID NO: 51, respectively; or the CDR1, the CDR2, and the CDR3 may comprise an amino acid sequence as set forth in SEQ ID NO: 8, SEQ ID NO: 29, and SEQ ID NO: 52, respectively; or the CDR1, the CDR2, and the CDR3 may comprise an amino acid sequence as set forth in SEQ ID NO: 9, SEQ ID NO: 30, and SEQ ID NO: 53, respectively; or the CDR1, the CDR2, and the CDR3 may comprise an amino acid sequence as set forth in SEQ ID NO: 10, SEQ ID NO: 31, and SEQ ID NO: 54, respectively; or the CDR1, the CDR2, and the CDR3 may comprise an amino acid sequence as set forth in SEQ ID NO: 11, SEQ ID NO: 32, and SEQ ID NO: 55, respectively; or the CDR1, the CDR2, and the CDR3 may comprise an amino acid sequence as set forth in SEQ ID NO: 12, SEQ ID NO: 33, and SEQ ID NO: 56, respectively; or the CDR1, the CDR2, and the CDR3 may comprise an amino acid sequence as set forth in SEQ ID NO: 13, SEQ ID NO: 34, and SEQ ID NO: 57, respectively; or the CDR1, the CDR2, and the CDR3 may comprise an amino acid sequence as set forth in SEQ ID NO: 14, SEQ ID NO: 35, and SEQ ID NO: 60, respectively; or the CDR1, the CDR2, and the CDR3 may comprise an amino acid sequence as set forth in SEQ ID NO: 15, SEQ ID NO: 36, and SEQ ID NO: 61, respectively; or the CDR1, the CDR2, and the CDR3 may comprise an amino acid sequence as set forth in SEQ ID NO: 16, SEQ ID NO: 37, and SEQ ID NO: 62, respectively; or the CDR1, the CDR2, and the CDR3 may comprise an amino acid sequence as set forth in SEQ ID NO: 17, SEQ ID NO: 38, and SEQ ID NO: 64, respectively; or the CDR1, the CDR2, and the CDR3 may comprise an amino acid sequence as set forth in SEQ ID NO: 18, SEQ ID NO: 39, and SEQ ID NO: 65, respectively; or the CDR1, the CDR2, and the CDR3 may comprise an amino acid sequence as set forth in SEQ ID NO: 19, SEQ ID NO: 42, and SEQ ID NO: 67, respectively; or the CDR1, the CDR2, and the CDR3 may comprise an amino acid sequence as set forth in SEQ ID NO: 20, SEQ ID NO: 43, and SEQ ID NO: 68, respectively; or the CDR1, the CDR2, and the CDR3 may comprise an amino acid sequence as set forth in SEQ ID NO: 21, SEQ ID NO: 44, and SEQ ID NO: 69, respectively.

For example, the VHH may comprise an amino acid sequence as set forth in any one of SEQ ID NOs: 70-104. For example, the SLN9056 comprises an amino acid sequence as set forth in SEQ ID NO: 70. For example, the SLN9057 comprises an amino acid sequence as set forth in SEQ ID NO: 71. For example, the SLN0042 comprises an amino acid sequence as set forth in SEQ ID NO: 72. For example, the SLN0043 comprises an amino acid sequence as set forth in SEQ ID NO: 73. For example, the SLN0044 comprises an amino acid sequence as set forth in SEQ ID NO: 74. For example, the SLN0045 comprises an amino acid sequence as set forth in SEQ ID NO: 75. For example, the SLN0049 comprises an amino acid sequence as set forth in SEQ ID NO: 76. For example, the SLN0056 comprises an amino acid sequence as set forth in SEQ ID NO: 77. For example, the SLN0057 comprises an amino acid sequence as set forth in SEQ ID NO: 78. For example, the SLN0059 comprises an amino acid sequence as set forth in SEQ ID NO: 79. For example, the SLN0062 comprises an amino acid sequence as set forth in SEQ ID NO: 80. For example, the SLN0064 comprises an amino acid sequence as set forth in SEQ ID NO: 81. For example, the SLN0065 comprises an amino acid sequence as set forth in SEQ ID NO: 82. For example, the SLN0071 comprises an amino acid sequence as set forth in SEQ ID NO: 83. For example, the SLN0072 comprises an amino acid sequence as set forth in SEQ ID NO: 84. For example, the SLN0046 comprises an amino acid sequence as set forth in SEQ ID NO: 85. For example, the SLN0058 comprises an amino acid sequence as set forth in SEQ ID NO: 86. For example, the SLN9008 comprises an amino acid sequence as set forth in SEQ ID NO: 87. For example, the SLN9013 comprises an amino acid sequence as set forth in SEQ ID NO: 88. For example, the SLN9015 comprises an amino acid sequence as set forth in SEQ ID NO: 89. For example, the SLN9025 comprises an amino acid sequence as set forth in SEQ ID NO: 90. For example, the SLN9026 comprises an amino acid sequence as set forth in SEQ ID NO: 91. For example, the SLN9056 comprises an amino acid sequence as set forth in SEQ ID NO: 70.

The antigen binding protein of the present application may compete with the reference antibody to bind to the Tf, wherein the reference antibody may include a heavy chain variable region and a light chain variable region, the heavy chain variable region of the reference antibody may include HCDR1, HCDR2 and HCDR3, the HCDR1 may include an amino acid sequence as set forth in any one of SEQ ID NOs: 1-21, the HCDR2 may include an amino acid sequence as set forth in any one of SEQ ID NOs: 22-44, and the HCDR3 may include an amino acid sequence as set forth in any one of SEQ ID NOs: 45-69.

Polypeptide

In another aspect, the present application provides a polypeptide which comprising the transferrin-binding protein.

For example, the polypeptide may comprise a therapeutic entity.

For example, the therapeutic entity may be an engineered cytotoxic *Pseudomonas* exotoxin A (PE38). For example, the PE38 may comprises an amino acid sequence as set forth in SEQ ID NO: 109.

For example, the therapeutic entity may be a glucagon-like peptide-1 (GLP-1) or its variant. For example, the GLP-1 may comprises an amino acid sequence as set forth in SEQ ID NO: 108.

For example, the variant may be a polypeptide that has significant sequence identity with the parent polypeptide and retain the biological activity of the parent polypeptide. For example, the amino acid sequence of variant may have at least about 50%, 75%, 80%, 90%, 95%, 96%, 97%, 98%, 98.2%, 98.4%, 98.6%, 98.8%, 99%, 99.1%, 99.2%, 99.3%, 99.4%, 99.5%, 99.6%, 99.7%, 99.8%, 99.9% or more identity with the amino acid sequence of the parent polypeptide. For example, the variant may also be a protein or polypeptide with one or more amino acids substituted, deleted or added to the amino acid sequence of the protein and/or the polypeptide. For example, the variant may include a protein or polypeptide that has amino acid changes by at least one, such as 1-30, 1-20 or 1-10, and also such as 1, 2, 3, 4 or 5 amino acid substitution, deletion and/or insertion. For example, the substitution may be conservative.

For example, the therapeutic entity and the transferrin-binding protein may be directly linked.

For example, the therapeutic entity and the transferrin-binding protein may be linked through gene fusion or recombinant DNA technologies.

For example, the therapeutic entity and the transferrin-binding protein may be indirectly linked.

For example, the therapeutic entity and the transferrin-binding protein may be linked through a spacer.

For example, the therapeutic entity and the transferrin-binding protein may be linked through a linker.

For example, the linker may be a peptide with amino acid sequence.

For example, the linker may be derived from artificial synthesis.

Isolated Nucleic Acid Molecules, Vector, Cell

In another aspect, the present application provides one or more isolated nucleic acid molecules encoding the isolated transferrin-binding protein of the present application or the polypeptide.

The nucleic acid molecule of the present application may be isolated. For example, it may be produced or synthesized by the following methods: (i) amplified in vitro, for example produced by polymerase chain reaction (PCR) amplification, (ii) produced by cloning and recombination, (iii) purified, for example by enzyme digestion and gel electrophoresis fractionation, or (iv) synthesized, for example chemically synthesized. In certain embodiments, the isolated nucleic acid is a nucleic acid molecule prepared by a recombinant DNA technology.

In the present application, the nucleic acid encoding the antibody or an antigen-binding fragment thereof may be prepared by a variety of methods known in the art, including but not limited to restriction fragment operation or overlap extension PCR employing synthetic oligonucleotides.

In another aspect, the present application provides a vector which may include the nucleic acid molecule of the present application.

In another aspect, the present application provides one or more vectors including one or more nucleic acid molecules of the present application. Each vector may contain one or more of the nucleic acid molecules. Furthermore, the vector may also contain other genes, e.g., a marker gene that allows selection of the vector in an appropriate host cell and under appropriate conditions. Furthermore, the vector may also contain an expression control element that allows a coding region to be correctly expressed in an appropriate host. Such a control element is well known to those skilled in the art, and may include, for example, a promoter, a ribosome binding site, an enhancer, and other control elements that regulate gene transcription or mRNA translation. The one or more nucleic acid molecules of the present application may be operably linked to the expression control element. The vector may include, for example, a plasmid, a cosmid, a virus, a phage, or other vectors commonly used in, for example, genetic engineering. For example, the vector is an expression vector.

In another aspect, the present application provides a cell which may include the nucleic acid molecule of the present application or the vector of the present application.

In another aspect, the present application provides a host cell, which may include one or more nucleic acid molecules of the present application and/or one or more vectors of the present application.

In certain embodiments, each kind of or each host cell may include one or one kind of nucleic acid molecule or vector of the present application. In certain embodiments, each kind of or each host cell may include multiple (e.g., 2 or more) or multiple kinds of (e.g., 2 or more kinds of) nucleic acid molecules or vectors of the present application. For example, the vector of the present application may be introduced into the host cell, e.g., a eukaryotic cell, such as a cell from a plant, a fungal cell or a yeast cell, etc. The vector of the present application may be introduced into the host cell by a method known in the art, such as electroporation, lipofectine transfection, lipofectamin transfection, and the like.

Pharmaceutical Composition

In another aspect, the present application provides a pharmaceutical composition which may include the transferrin-binding protein of the present application, the nucleic acid molecule of the present application, the vector of the present application and/or the cell of the present application, and optionally a pharmaceutically-acceptable adjuvant.

For example, the pharmaceutical composition of the present application may be directly used for therapeutic or diagnosis, and thus may be used for preventing and treating diseases Furthermore, other therapeutic entities may be used at the same time.

The pharmaceutical composition of the present application may contain a safe and effective amount (e.g., 0.001-99 wt %, 0.01-90 wt %, or 0.1-80 wt %) of the transferrin-binding protein of the present application and a pharmaceutically-acceptable adjuvant (which may include a carrier or excipient). Such a carrier may include, but are not limited to, saline, a buffer, glucose, water, glycerol, ethanol, and a combination thereof. A pharmaceutical preparation should be matched with the mode of administration. The pharmaceutical composition of the present application may be made into an injection form, for example, it may be prepared by a conventional method with physiological saline or an aqueous solution containing glucose and other adjuvants. The pharmaceutical composition, such as an injection or a solution, should be manufactured under aseptic conditions. The administration amount of the active ingredient is a therapeutically effective amount. Moreover, the transferrin-binding protein of the present application may also be used together with other therapeutic entities.

The transferrin-binding protein or pharmaceutical composition described herein may be formulated, administered and administered in a manner consistent with good medical practice. Considerations in this case include a specific condition being treated, a specific mammal being treated, the clinical symptoms of an individual patient, the etiology of a condition, a drug delivery site, an administration method, and other factors known to medical practitioners. A therapeutic entity needs not, but is optionally formulated together with and/or administered simultaneously with one or more entities currently used for preventing or treating the condition under consideration. The effective amount of such other entities depends on the amount of the therapeutic agent present in the preparation, the type of condition or treatment, and other factors discussed above. Generally, these entities may be used at any dose determined empirically/clinically as appropriate and by any route determined empirically/clinically as appropriate. Compared with single therapy, the dose of the antibody administered in the combined therapy may be reduced. It is easy to monitor the progress of this therapy by conventional techniques.

The Method

In another aspect, the present application the present application provides one method to translocate a molecule across cellular membrane by using a transferrin-binding protein.

For example, the method may be used for drug delivery across cellular membrane.

For example, the cellular membrane may belong to a polarized cell.

For example, the polarized cell may be a functional cell.

For example, the polarized cell may be a nerve cell.

For example, the cellular membrane may belong to a unpolarized cell.

For example, the unpolarized cell may be a nerve cell.

For example, the unpolarized cell may transmit nerve signals.

For example, the polarized and/or unpolarized cell may express transferrin receptor on its cellular membrane.

For example, the polarized and/or unpolarized cell may express human transferrin receptor on its cellular membrane.

For example, the polarized and/or unpolarized cell may express transferrin receptor 1.

For example, the polarized and/or unpolarized cell may express human transferrin receptor 1.

For example, the unpolarized cell may belong to blood brain barrier.

For example, the unpolarized cell may belong to intestinal epithelium.

For example, the unpolarized cell may belong to multiple layers of cells in a solid tissue.

In the present application, the method of drug delivery across cellular membrane may comprise crossing blood brain barrier, crossing intestinal epithelium, crossing multiple layers of cells in a solid tissue, intracellular delivery of drug, and/or recycling of an endocytosed drug back to circulation.

For example, the drug delivery across cellular membrane may belong to an unpolarized cell.

For example, the drug delivery across cellular membrane may comprise crossing blood brain barrier of central nervous system-targeted systemically dosed drug.

For example, the drug delivery across cellular membrane may comprise crossing intestinal epithelium of orally administered drug.

For example, the drug delivery across cellular membrane may comprise penetration of drug through multiple layers of cells in a solid tissue.

For example, the drug delivery across cellular membrane may belong to a polarized cell.

For example, the drug delivery across cellular membrane may comprise intracellular delivery of drug.

For example, the drug delivery across cellular membrane may comprise recycling of an endocytosed drug back to circulation.

For example, the drug may comprise a small molecular compound.

For example, the small molecular compound may be a chemically synthesized drug.

For example, the molecular weight of the small molecular compound may be less than 1000 Daltons.

For example, the small molecular compound may have a therapeutic effect.

For example, the small molecular compound may have anti-tumor activity.

For example, the drug may comprise a synthetic peptide.

For example, the synthetic peptide may comprise α-amino acid.

For example, the α-amino acid may be linked through peptide chain.

For example, the synthetic peptide may be synthesized through solid phase peptide synthesis.

For example, the synthetic peptide may be synthesized through liquid phase peptide synthesis.

For example, the drug may comprise a recombinant protein.

For example, the recombinant protein may be a semi-synthetic or synthetic origin polypeptide.

For example, the recombinant protein may be expressed by using recombinant DNA technology to connect DNA molecules from different sources.

For example, the recombinant protein may be no longer fully or partially associated with the protein in natural state.

For example, the recombinant protein may be linked to a peptide other than the peptide linked in its natural state.

For example, the recombinant protein may not exist in the natural state.

For example, the drug may comprise an antibody. For example, the drug may comprise an antibody fragment.

For example, the antigen fragment may be a Fab, a Fab', a F(ab)2, a Fv fragment, a F(ab')2, a scFv, a di-scFv and/or dAb.

For example, the drug may comprise an enzyme.

For example, the enzyme may be a catalytically active protein.

For example, the drug may comprise a piece of nucleotide acid sequence.

For example, the nucleotide acid sequence may be a DNA sequence.

For example, the nucleotide sequence may be an RNA sequence.

For example, the nucleotide sequence may be genomic DNA, cDNA, synthetic DNA, proviral DNA, viral DNA, mRNA, synthetic RNA or a combination thereof.

For example, the nucleotide sequence may encode peptide or protein.

For example, the synthetic RNA may modulate mRNA stability or translation.

For example, the synthetic RNA could be small interfering RNA (siRNA) or antisense oligoes (ASO).

For example, the drug may comprise a liposome.

For example, the liposome may be a vesicle composed one or more layers of concentrically arranged lipid bilayers.

For example, the liposome may comprise a water phase.

For example, the water phase may comprise nucleic acid.

For example, the drug may comprise a nano-sized particles such as lipid nanoparticle.

For example, the lipid nanoparticle may contain multiple lipid molecules physically bound to each other by intermolecular forces.

For example, the intermolecular forces may be covalent or non-covalent.

For example, the lipid nanoparticle may comprise one or more lipids.

For example, the lipids may be cationic lipids, non-cationic lipids and PEG-lipids.

For example, the drug may comprise a drug vehicle.

For example, the drug vehicle may be a standard composition suitable for human administration.

For example, the drug vehicle may be a typical adjuvant used in animal vaccination.

For example, the drug may comprise a modified virus.

For example, the modified virus may be a genetically engineered virus.

For example, the modified virus may inhibit the growth of cancerous or hyperproliferative cells in vivo or in vitro.

For example, the modified virus may induce death on cancerous or hyperproliferative cells in vivo or in vitro.

For example, the modified virus may be an oncolytic virus.

For example, the drug may comprise a gene-therapy vector.

For example, the gene-therapy vector may be capable of delivering the target gene into the target cell.

For example, the target gene may be released in the target cell.

For example, the target gene may be integrated into the nucleus.

For example, the gene-therapy vector may exert the therapeutic function of the target gene.

For example, the gene-therapy vector may be a plasmid vector, a phage vector, a viral vector or a non-viral vector thereof.

For example, the gene-therapy vector may be a cloning vector or an expression vector thereof.

For example, the gene-therapy vector may be a temperature sensitive vector, a fusion expression vector or a non-fusion expression vector thereof.

For example, the drug may be associated to the transferrin-binding protein.

For example, the dug may be associated to the transferrin-binding protein through genetic fusion.

For example, the drug may be associated to the transferrin-binding protein through chemical conjugation.

For example, the method may be used for extending half-life in circulation of a therapeutic entity.

For example, the therapeutic entity may be linked with the transferrin-binding protein directly or indirectly.

For example, the method may be used for delivering a therapeutic drug to transferrin receptor-expressing cells or organs, comprising or using a transferrin-binding entity.

For example, the method may be used for delivering a targeted drug to cross blood-brain barrier, intestinal epithelium and/or cell membranes that express transferrin receptor, comprising using a transferrin-binding entity.

For example, the method may be used for oral delivery of a therapeutic or diagnostic entity, the therapeutic or diagnostic entity is linked with the antigen binding protein.

For example, the method may be used for intracellular delivery of a therapeutic entity, the therapeutic entity is linked with the antigen binding protein directly or indirectly.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); CPU, colony forming units; rpm, revolutions per minutes; RT, room temperature; i.m., intramuscular(ly); i.p., intraperitoneal(ly); s.c., subcutaneous(ly); and the like.

Example 1 Establishment of VHH Immune Library

Human transferrin (human transferrin, Sigma T3309) was used to immunize two healthy and age-appropriate camels for 4 times. After the antibody tilter was qualified, 200 ml of peripheral blood was taken from each, lymphocytes were separated, and total RNA was extracted. Reverse transcription was applied to create cDNA for construction of a phage-displayed camel immune VHH antibody library. To check the quality of the VHH antibody library, 24 independent phage clones were subjected to DNA sequencing. The data indicated that 22 out of 24 clones contain standard VHH sequences fused to gp3 protein that was used for phage display, and each of the 22 clones had a unique VHH sequence with a CDR3 of 9 or more amino acids in length. This library was used for subsequent antibody discovery.

Example 2 VHH Discovery 2.1—Panning

The phage library was taken out from −80° C. freezer, incubated at 37° C. for 10 min, and centrifuged at 5000 rpm for 5 min. $10^{12}$~$10^{13}$ CFU phages (input) were transferred to 1 mL of PBS solution with 1% BSA, 10 μg of biotinylated human or mouse transferrin protein in a microtube. The mixture was incubated at RT for 1 h before 100 μL suspension of streptavidin-coated magnetic Dyna-beads were added. After incubation at RT for 30 min on a rotating tumbler, the tube was placed on a magnetic rack for 30 s to remove the solution mixture. The beads were washed with 1 mL of PBST (0.05% Tween 20 in PBS, pH7.4) for 10 times before a final wash with PBS.

Phages were eluted off the beads with 1 mL of 10 μg/mL trypsin in PBS by incubating at 37° C. for 30 min and separated from the beads on a magnetic rack. The supernatant (output) were transferred to a tube containing 4 mL TG1 (A600≈0.6) to infect the bacteria. After incubation at 37° C. for 30 min, the infected bacteria were collected by centrifugation at 4,500 rpm for 10 min at 4°. The pellet was resuspended in 500 μL and spread onto 25×25 cm 2×YT/Amp/Glu plate to amplify the phage-infected bacteria. After being incubated overnight at 37° C., the bacteria were scraped from the plate by adding 30 mL of 2×YT medium, and collected by centrifugation at 4,500 rpm for 10 min. The pellet was resuspended by adding 2 mL 2×YT medium containing 40% glycerol to have stocks at −80° C., or directly prepare phages (as below in phage preparation or packaging) for the next round of panning as needed.

Input and output phages were also titrated to determine phage enrichment efficiency of the panning process. Briefly, serial dilutions in PBS (10-fold, generally $10^{-1}$~$10^{-9}$) of the input/output phages were prepared, 10 μL of the serially diluted phages was mixed with 90 μL of log-phase TG1 in a new tube before incubation at 37° C. for 30 min. Thereafter, 10 μL of the mixture were spotted onto pre-warmed 2×YT/Amp plate. The lid was left open to evaporate solution before the bacteria plates were cultured at 37° C. O/N. Colonies were counted and titer was calculated for input and output phages respectively, ratio of the output/input from each round of panning were used to determine efficiency of the panning process.

2.2 Phage Preparation or Packaging

The phage-infected TG1 bacteria were inoculated with 2×YT/Amp/Glu medium at 37° C. with shaking (250 rpm) to reach an A600 of 0.6 (approximately 1-2 h). Helper phage M13K07 were added at a phage:bacteria ratio of 1000. The culture was incubated at 37° C. without shaking for 30 min, followed by 30 min with shaking at 180 rpm.

The bacterial cultures were centrifuged in sterilized centrifuge bottles at 4,500 rpm for 10 min to recover the bacterial pellets. The bacterial pellets were resuspended in 100 mL 2×YT/Amp/Kan (Amp:100 μg/mL, Kan:50 μg/mL) and transferred into a 250 mL flask for incubation with shaking (250 rpm) for 4 h at 37° C.

The culture was centrifuged at 4,500 rpm for 10 min to collect supernatant. Phages were precipitated from the supernatant by adding ¼ volume of PEG solution (20% Polyethylene glycol 6000, 2.5 M NaCl) and incubation on ice overnight. After being collected by centrifugation at 4,500 rpm for 30 min at 4° C., the phage pellets were resuspended in 5 mL of PBS and incubated with shaking at 37° C. for 30 min. Insoluble debris was removed by centrifugation at 4,500 rpm for 10 min, and the soluble phages in supernatant were transferred to a new tube to repeat PEG precipitation once. The final phage solution in PBS was used for the next round of panning or mixed with glycerol for storage at −80° C.

2.3 Phage-Based ELISA Screening

Single colonies from panning outputs were individually picked from argar plates and inoculated with 2×YT/GA medium (2% Glucose, 100 μg/mL Ampicillin) in 96-well deep well plates at 37° C. overnight, with a shaking speed at 320 rpm. 10 μL of the overnight culture were transferred to 400 μL of 2YT/GA medium in a new deep-well plate. The culture grew at 37° C. with shaking (800 rpm) to an A600 of 0.6 (approximately 1 h), before helper phage M13K07

(4.2×10$^{13}$ CFU/mL) was added at a phage:bacteria ratio of 1000 (100 μL in 100 mL). The culture were kept incubation at 37° C. without shaking for 30 min, followed by 30 min with shaking at 180 rpm. The bacterial cultures were centrifuged at 4,000 rpm for 30 min to discard the supernatant. The bacterial pellets were resuspended in 400 μL 2×YT/AK (Amp:100 μg/mL, Kan:50 μg/mL), and cultured with shaking (320 rpm) at 30° C. overnight. The bacterial cultures were centrifuged at 4,000 rpm for 30 min to collect the supernatant. The supernatant was used as phage solution for ELISA screening.

To conduct ELISA screening, 96-well microtiter plates were coated with 100 μL per well of Streptavidin at the concentration of 1 μg/mL (carbonate buffered saline or CBS at pH9.4) overnight at 4° C. Each well was blocked with 200 μL of blocking buffer (PBS pH7.4/0.05% Tween20/1% BSA) at RT for 1 h. the wells were washed 3 times with PB ST (PBS/0.05% Tween20, pH7.4) before 100 μL of biotinylated human or mouse transferrin protein (1 μg/mL in blocking buffer) were added and incubated at RT for 1 h. The wells were washed 3 times with PB ST before 100 μL of the phage solution (above) was added and incubated at RT for 1 h. The wells were washed 3 times with PBST, 100 μL of mouse anti-M13 IgG-HRP (prepared in blocking buffer) was added to each well and incubated for 1 h RT. The wells were washed 3 times with PBST, 100 μL of TMB solution was added and incubated at RT for 15 min in dark. The plate was scanned at 450 nm after the reaction was terminated with 100 μL of stop solution. The positive clones with specific binding to transferrin were selected for DNA sequencing, unique VHH's were identified upon the deduced amino acid sequences.

2.4 Production of Recombinant VHH-OVA-his Proteins

Unique VHH clones were selected for subcloning to create recombinant plasmids to produce VHH-OVA-His proteins (OVA comprises an amino acid sequence as set forth in SEQ ID NO: 107). After the plasmid sequence was verified by sequencing, small scale production of recombinant proteins was performed using transient transfection of HEK293 cells with the recombinant plasmid using lipofectamine or PEI as transfection reagent. Cultures were grown in shaking flasks media at scales ranging from 30 ml to 100 ml for 5-7 days. Cells were removed by centrifugation and culture supernatants were used for protein purification by Ni-NTA sepharose. The purified proteins were analyzed with 4-12% gradient SDS-PAGE gel under non-reducing or reducing conditions (FIG. 1).

2.5 Transferrin-Binding Assays

Figure 2A:
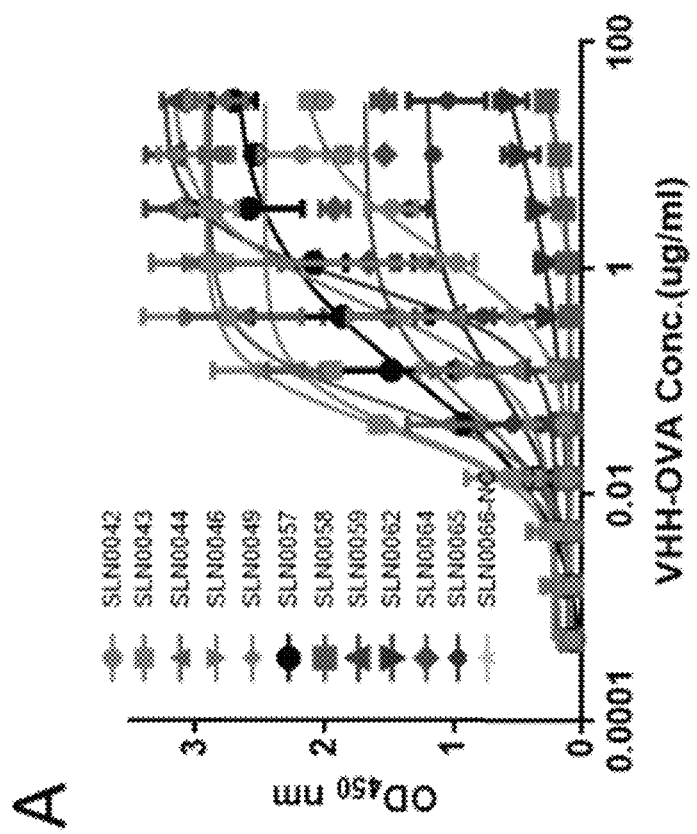
FIG. 2A-2B illustrates representative transferrin-mediated binding of the selected transferrin binding protein-OVA-His proteins to human transferrin at pH7.4 or pH6.0.
Figure 2B:
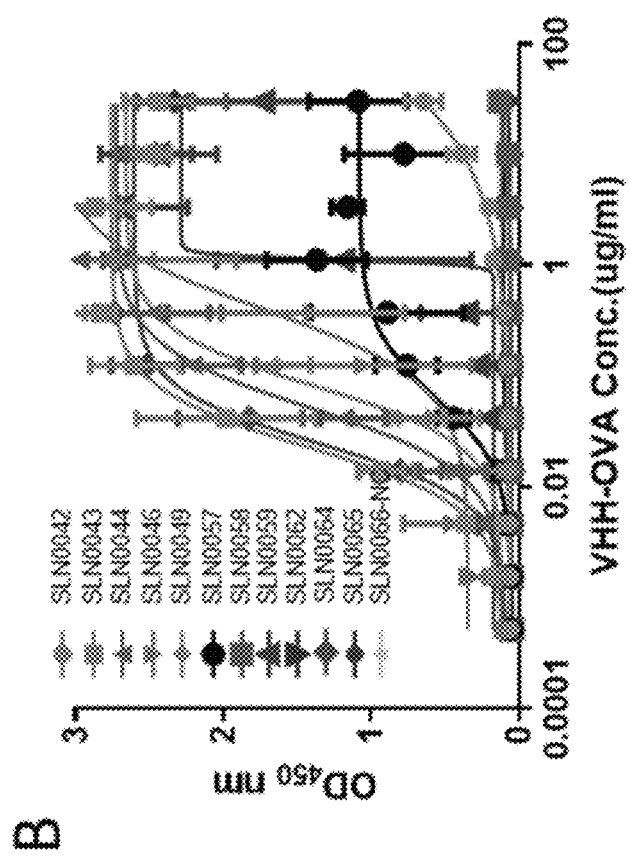

To test the recombinant proteins regarding transferrin binding capability and specificity, 96-well microplates were coated with streptavidin (1 μg/ml in CBS, 100 μl/well) and incubated at 4° C. overnight. After 3 times of washing with PBST, the plates were blocked with 1% BSA in PBST at RT for 1 hr. After 3 times of washing with PBST, biotinylated human or mouse transferrin protein (1 ug/ml in PBS, 100 ul/well) was added and incubate at RT for 1 h. After 3 times of washing with PBST, the purified VHH-OVA-His proteins were added and incubated at RT for 1 h (serially diluted in PBS either pH7.4 or pH6.0, starting from 10 ug/ml, 100 ul/well). Rabbit anti-chicken egg albumin (OVA) and a secondary anti-rabbit IgG-HRP were incubated sequentially, before the plates were washed with PBST 3 times and incubated with substrate solution and stop solution as described above for phage ELISA. Representative data were shown in FIG. 2A (pH7.4, holo-transferrin) or FIG. 2B (pH6.0, apo-transferrin) to illustrate binding activities of the recombinant VHH-OVA-His to the native human transferrin (Sigma).

Figure 3A:
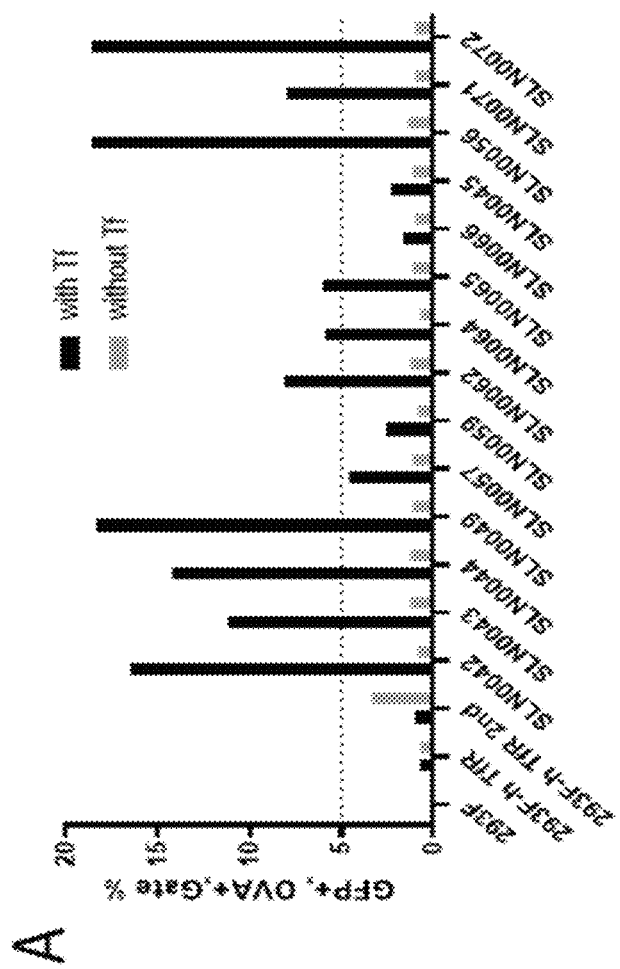
Figure 3B:
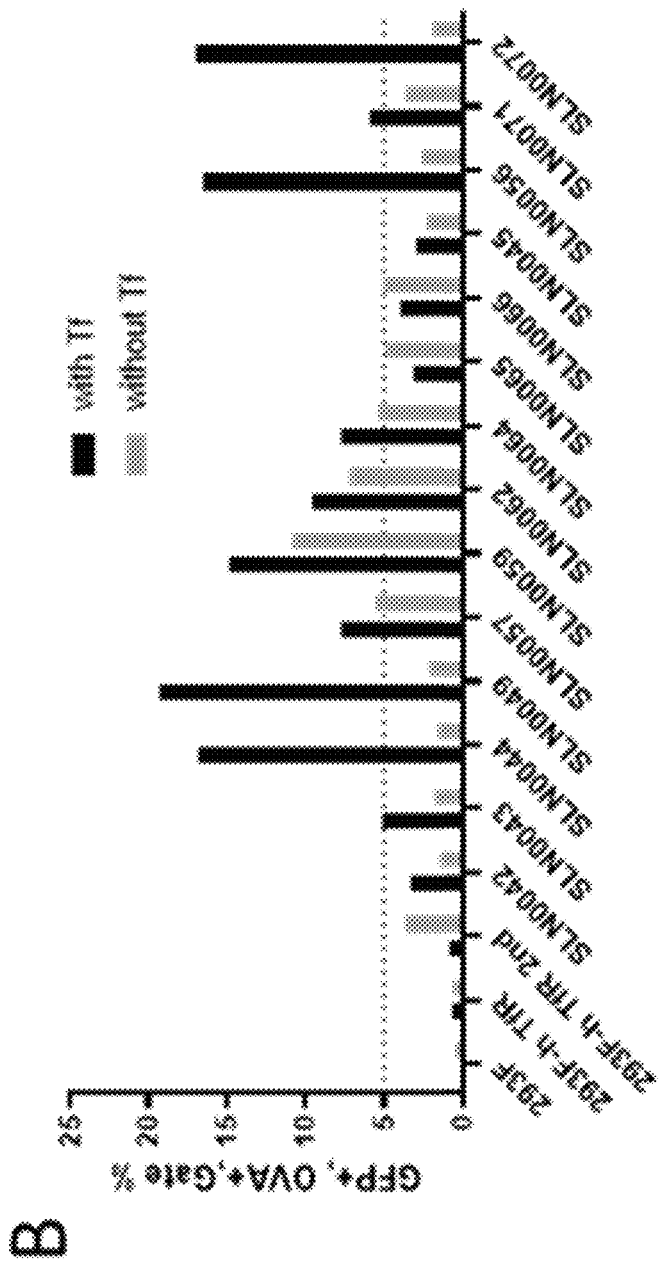
Figures 1, 3C:
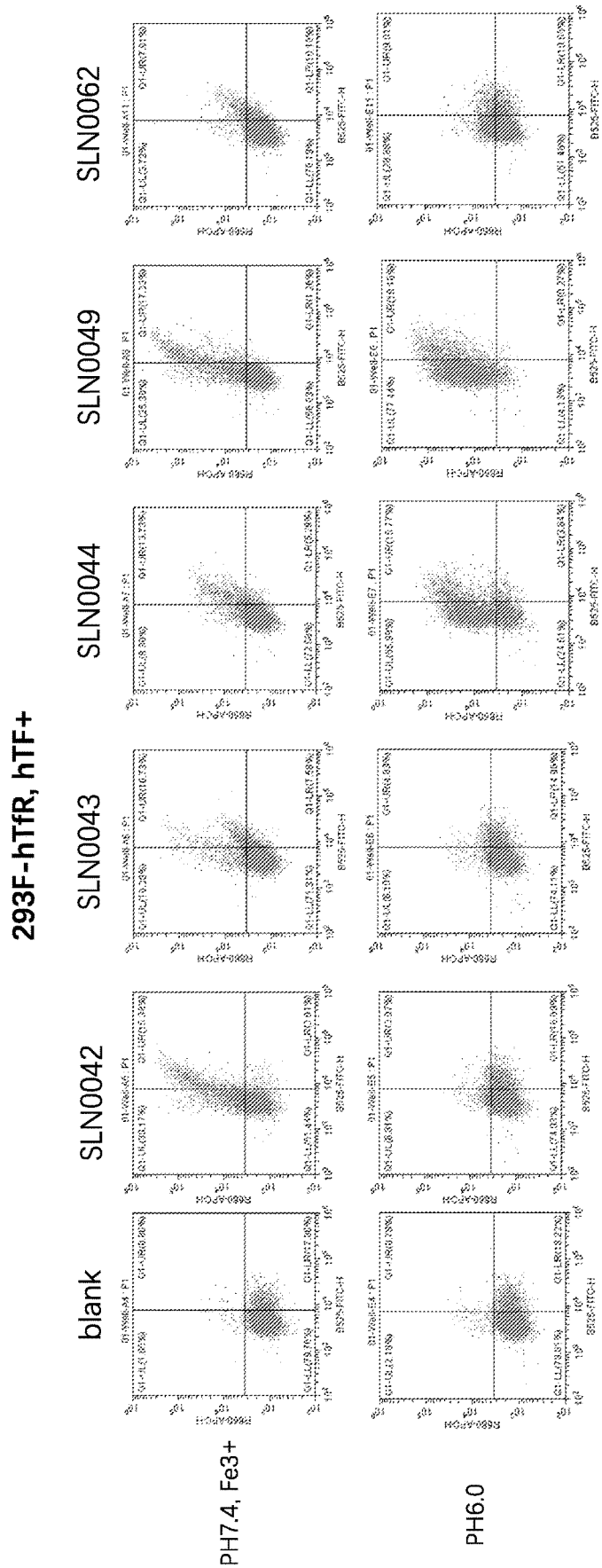

2.6 VHH-Binding Did not Disturb Transferrin/TfR1 Interaction on HEK293F-hTFR1 Cells HEK293F-hTfR1 cells were prepared by transfecting hTfR1-expressing plasmid, with a GFP tag, into HEK293F cells. Stable pool was used for this assay. Briefly, the engineered HEK293F cells expressing hTfR1 were cultured with OPM-293 CD05 medium at 37° C., with 8% CO 2 and saturated humidity in cell shaker. After the HEK293F-hTfR1 cells were harvested, counted and blocked with blocking buffer at 37° C. for 30 min, 1×10$^6$ of cells were used per reaction and mixed with VHH-OVA-His or a control protein solutions (final concentration at 10 μg/mL), with or without transferrin (final 5 μg/mL), with or without ironic citrate solution (final 0.2 mg/mL), at pH7.4 or pH6.0. The cells were washed twice by centrifugation at 300 g for 5 min at 4° C., before rabbit anti-OVA antibodies and a secondary anti-rabbit IgG-AF647 (all prepared in blocking buffer). The cells were scanned with CytoFLEX (Beckman). Data were analyzed using CytoExpert 2.4 software to determine 1) differential binding of VHH-OVA-His proteins to cells (transferrin-binding does not interfere transferrin/TfR1 interaction on the cell surface); 2) dependency on transferrin (specificity to transferrin); 3) dependency on TfR1 (specificity to TfR1-mediated cell binding); 4) dependency on pH value and Fe3+ (specificity to iron-associated holo-transferrin or iron-free apo-transferrin). The data (below and FIG. 3) indicated that the selected transferrin-binding VHH's such as SLN0042, SLN0043, SLN0044, SLN0049, SLN0062, SLN0064, SLN0065, SLN0056, SLN0071 and SLN0072 did not interfere transferrin/TfR1 interaction and could be associated to TfR1 on cell surface only through binding to transferrin. The data also confirmed results from ELISA that showed that some selected VHH's had differential affinity to holo- and apo-transferrin.

TABLE 1

Summary of VHH/Tf binding profiles on different PH conditions on hTfR1 overexpressed cell surface.

| VHH Variants | pH 7.4 | pH 6.0 | Non-Specific binding (pH 6.0) |
|---|---|---|---|
| SLN0042 | +++ | − | − |
| SLN0043 | ++ | − | − |
| SLN0044 | ++ | +++ | − |
| SLN0049 | +++ | +++ | − |
| SLN0057 | − | + | + |
| SLN0059 | − | + | + |
| SLN0062 | + | + | + |
| SLN0064 | + | + | + |
| SLN0065 | + | + | − |
| SLN0066 | − | − | − |
| SLN0045 | − | − | − |
| SLN0056 | +++ | +++ | − |
| SLN0071 | + | + | − |
| SLN0072 | +++ | +++ | − |

Note:
+++ ≥ 15%;
15% > ++ ≥ 10%;
10% > + ≥ 5%;
− < 5% Binding 2.7 Epitope Binning Epitope binning was used to distinguish different "bin" with different proteins. Because the antibodies in different "bins" bind to different epitopes and show different functional characteristics.

Figure 4:
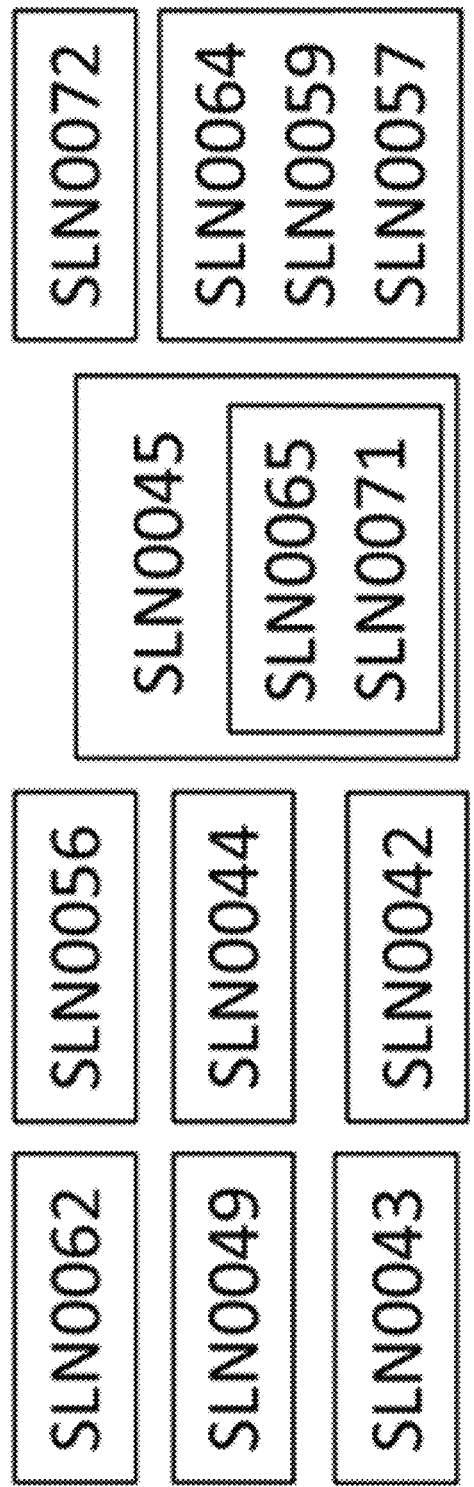
FIG. 4 illustrates epitope binning of representative transferrin binding protein of the present disclosure.
Figure 5A:
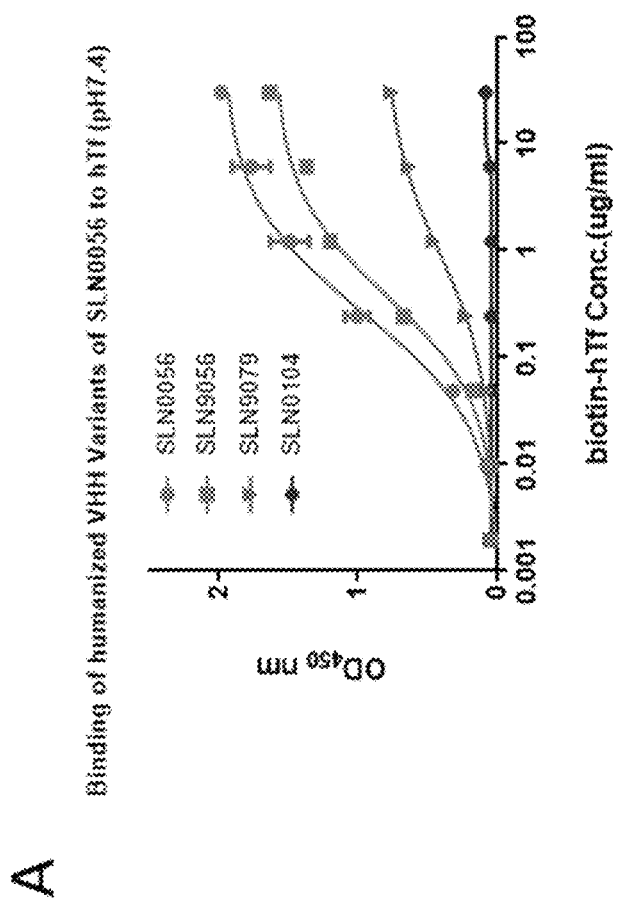
FIG. 5A-5D illustrates representative ELISA data show binding of the humanized transferrin binding protein variants to the native human transferrin at pH7.4 or pH6.0.
Figure 5B:
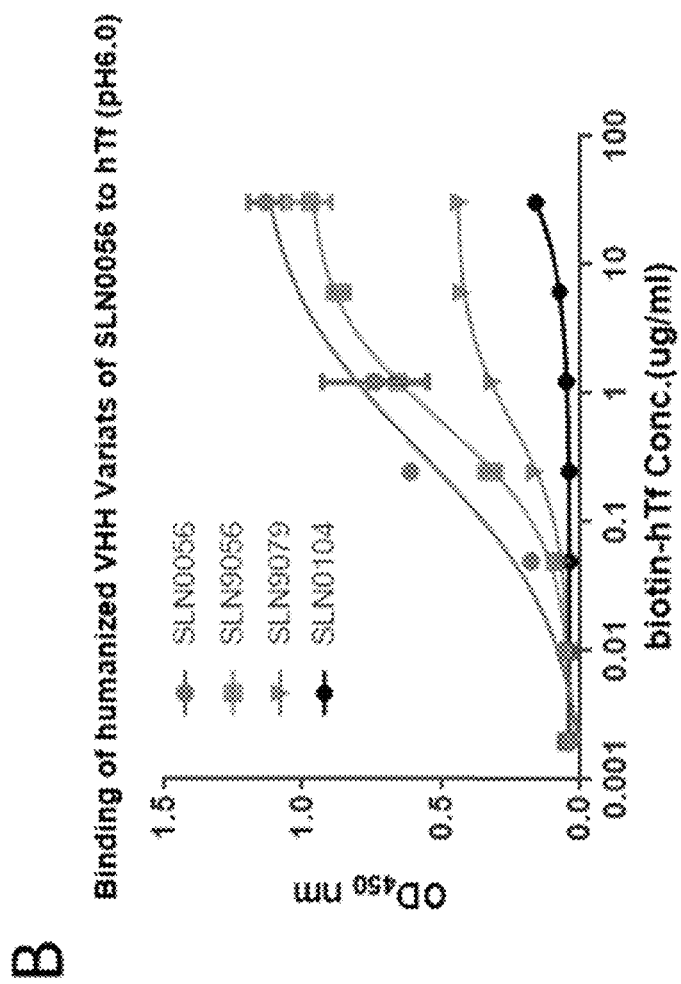
Figure 5C:
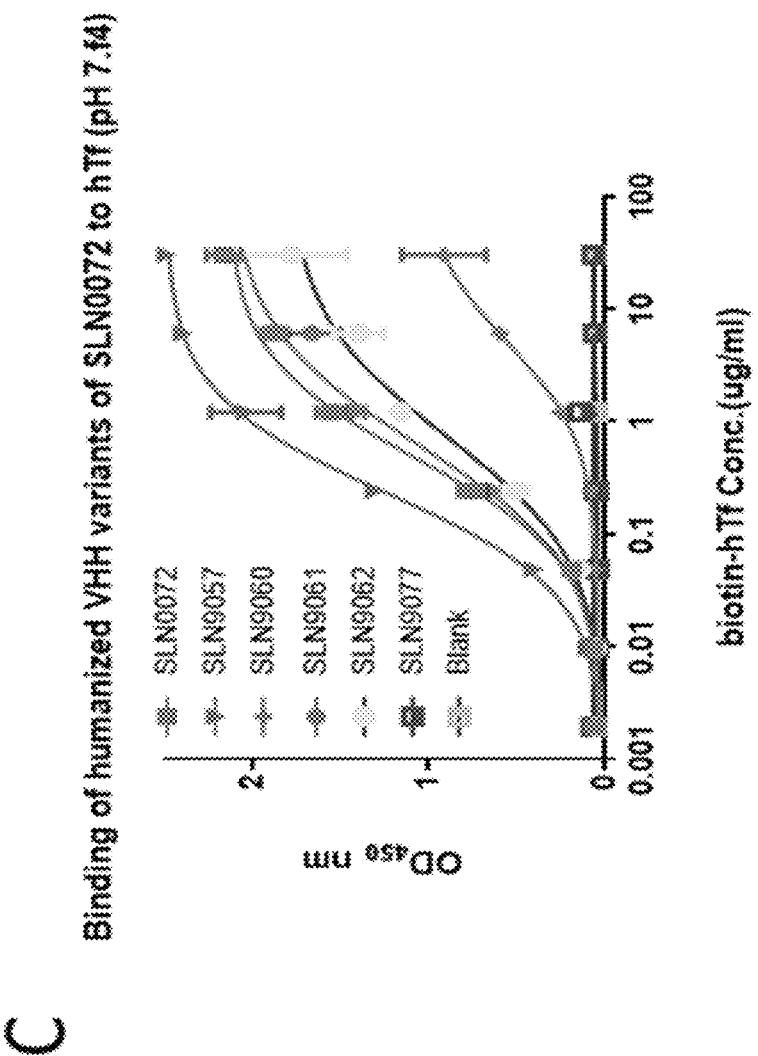
Figure 5D:
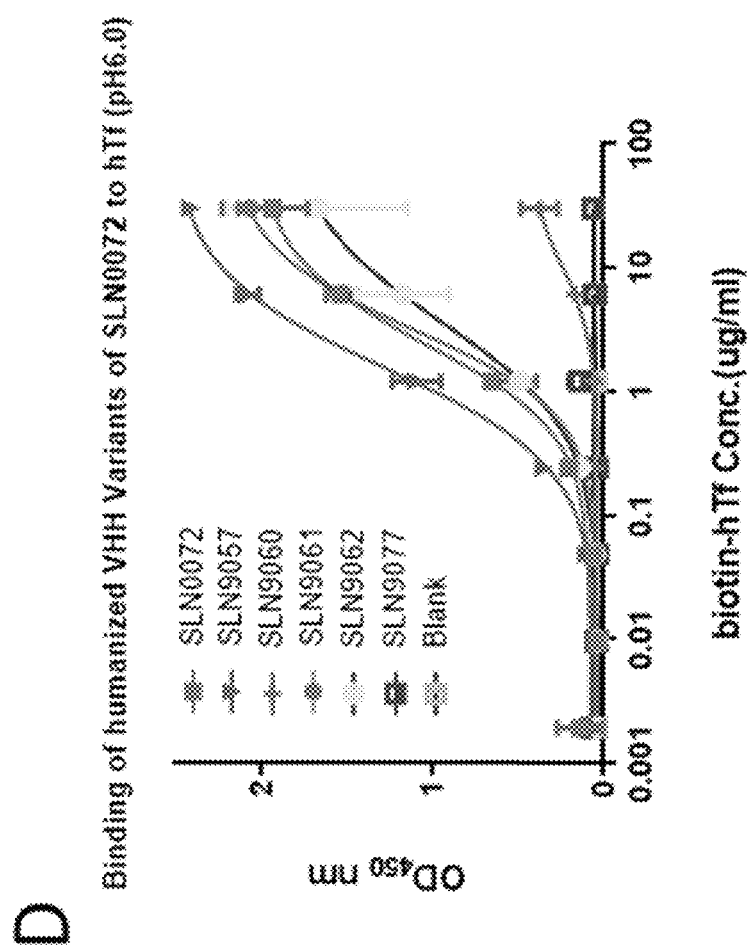
Figure 6A:
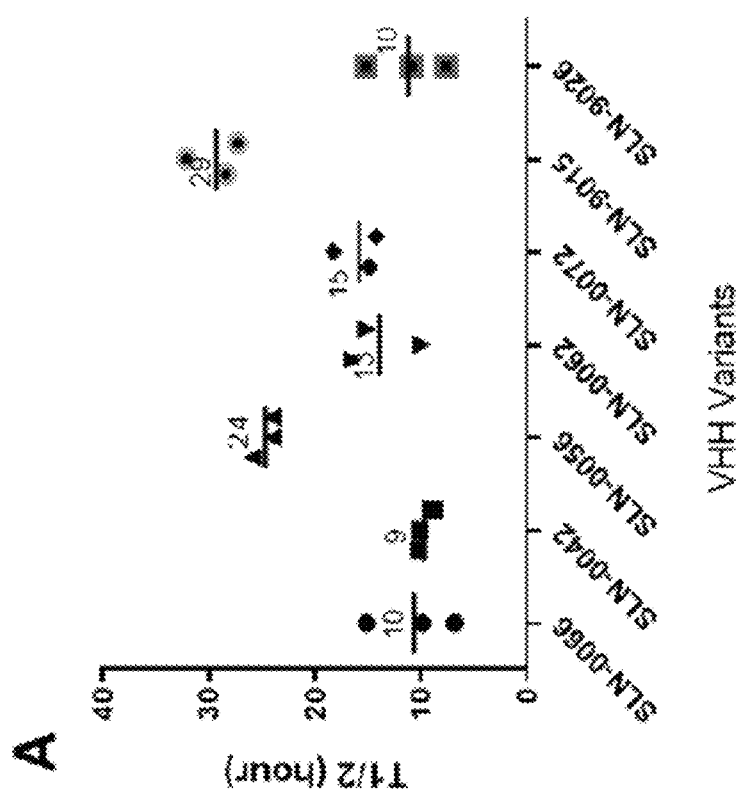
FIG. 6A illustrates circulation half-life of OVA fused to the transferrin binding protein of the present disclosure clones with different epitopes.
Figure 6B:
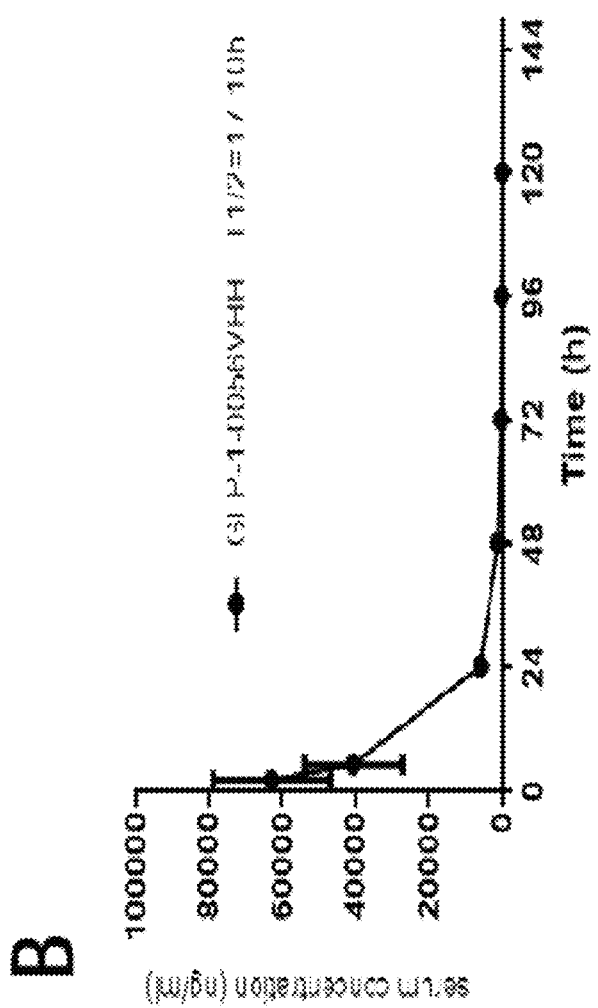
FIG. 6B illustrates circulation half-life of GLP-1-VHH in mice.
Figure 6C:
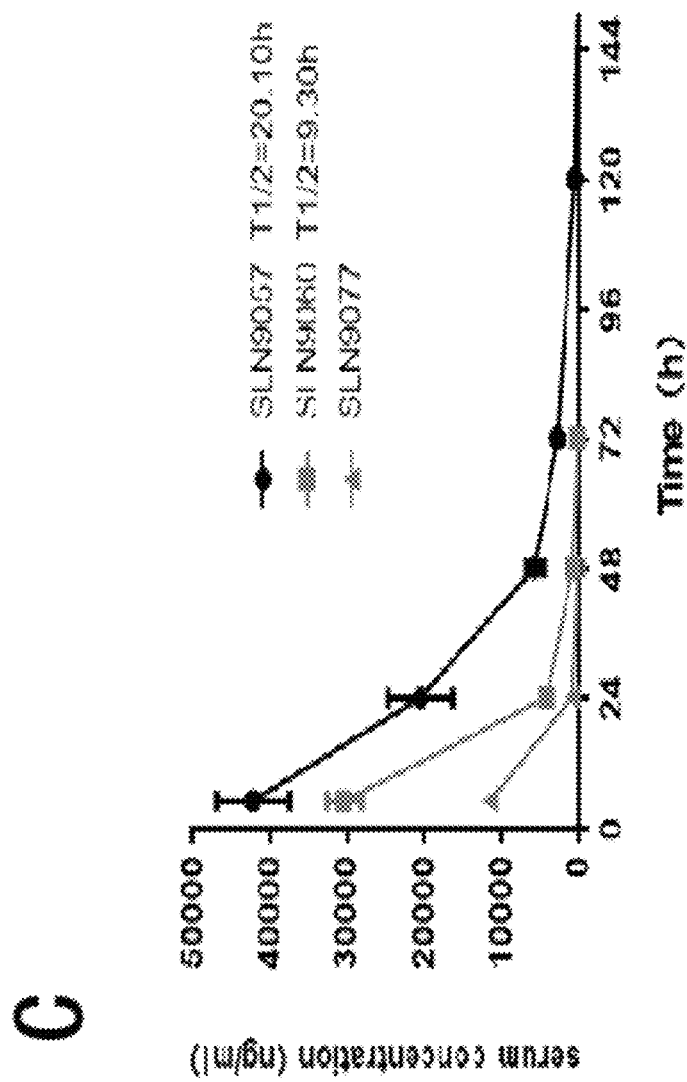
FIG. 6C illustrates VHH-enabled circulation half-life extension is affinity-dependent.

To conduct epitope binning, 96-well microplates were coated with 5 µg/mL of each VHH-OVA-His recombinant protein respectively (in CBS buffer, 100 µL/well) and incubated at 4° C. overnight. After washing and blocking as described above for ELISA, cross check board reactions were conducted by adding mixture of biotinylated human transferrin (final 1 µg/mL) and VHH-OVA-His protein (final 5 µg/mL) and incubated at RT for 1 h. The biotinylated transferrin binding to the VHH-OVA-His that were used for coating was detected with streptavidin-HRP and corresponding method. The data shown in FIG. 4 indicated that the selected VHH's belong to multiple bins, particularly different from reference antibodies (VHH1, VHH2, VHH3).

2.8 Transcytosis of VHH-OVA-his Proteins Across Monolayer of Caco-2 Cells

Caco-2 cells were seeded in 96-well trans-well plate at $2 \times 10^4$ per well and cultured for 12 days to allow formation of cellular monolayer in inner chamber (medium was changed in every other days during the first week and every day during the second week). On day 13, the monolayer cells were washed with prewarmed PBS and then incubated in MEM medium with 0.1% BSA without FBS at 37° C. for 30 min to remove the endogenous Tf. Recombinant VHH-OVA-His proteins (10 µg/mL) with or without native human transferrin (5 µg/mL), both prepared in MEM medium (pH 7.4) with 0.1% BSA were added into the inner chamber (above the monolayer of Caco-2 cells) and incubated for 2 h or 24 h at 37° C. Medium from the outer chamber were collected at the indicated time points for quantitative measurement with ELISA method, by referring standard curve developed by using the corresponding VHH-OVA-His proteins as control. Integrity of the Caco-2 cell monolayer was tested with Lucifer yellow (LY) rejection assay according to the manufacturer's instructions. Wells with more than 0.1% (basal level of passive crossing) of lucifer yellow signal from outer chamber signals compared to that of inner chamber would be considered as imperfect cellular monolayer for the measurement and thus discarded.

Quantitative ELISA measurement was conducted as procedures described above by using specific antibodies. Briefly, microplates were coated with rabbit anti-OVA polyclonal antibodies (5 µg/mL in CBS buffer), test articles or control (VHH-OVA-His protein) for standard curve were added, and detected with biotinylated anti-OVA antibodies and subsequent streptavidin-HRP conjugates. Standard curve was prepared by using recombinant VHH-OVA-His proteins serially diluted from 1000 ng/mL to 0 with a dilution factor of 3. The assay was qualified with inter-assay CV's less than 20% and recovery rate more than 90%.

Figure 7A:
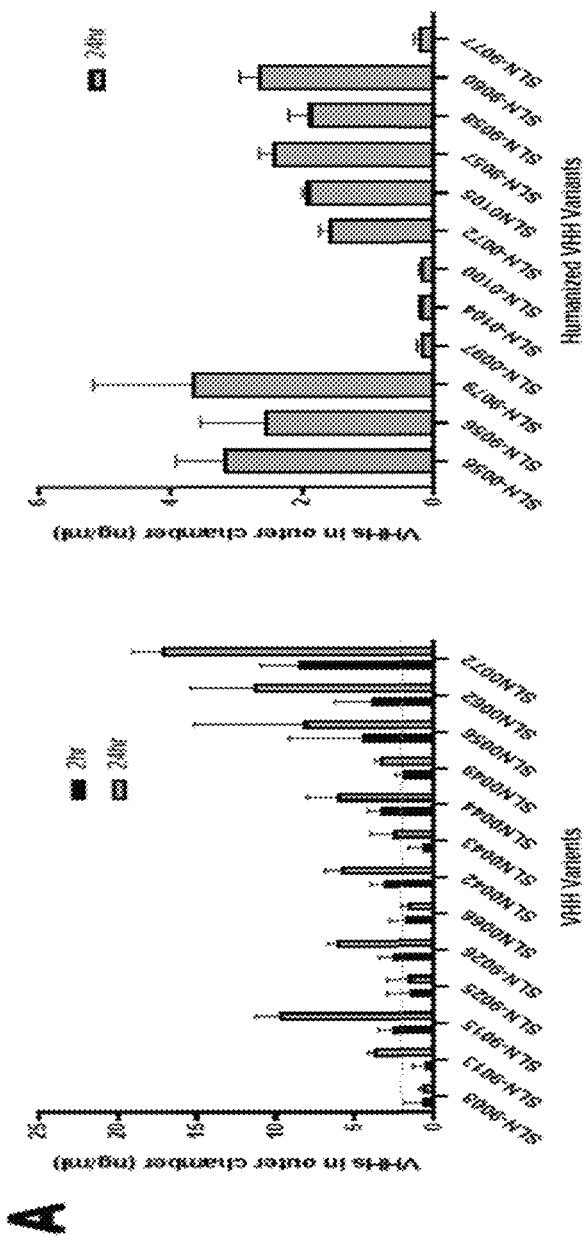
FIG. 7A-7C illustrates the transferrin binding protein enabled translocation of the fused OVA across monolayer of Caco-2 cells or through intestinal epithelium via transcytosis.
Figure 7B:
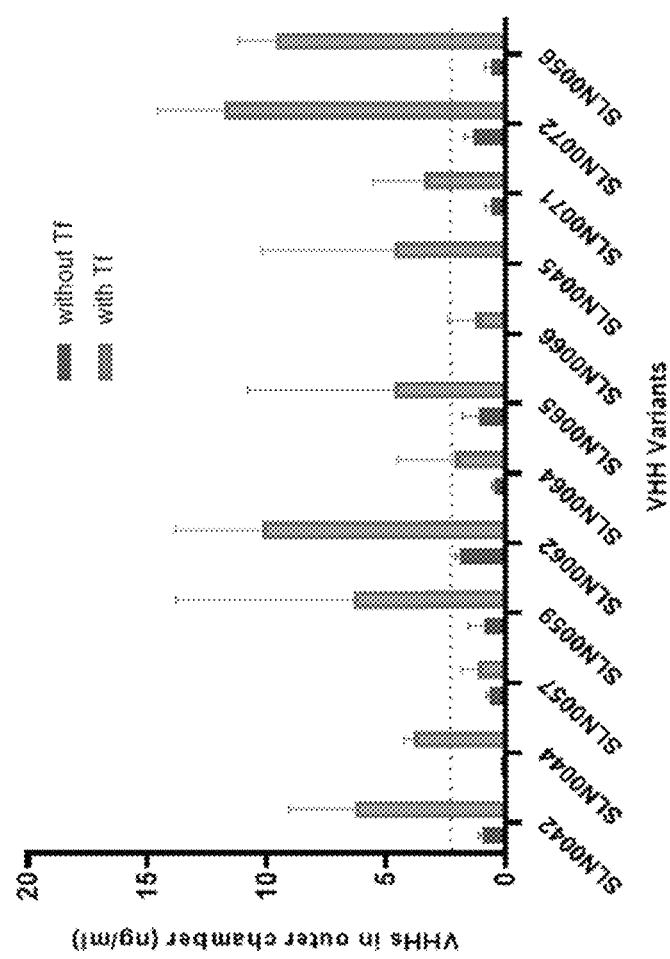
Figure 7C:
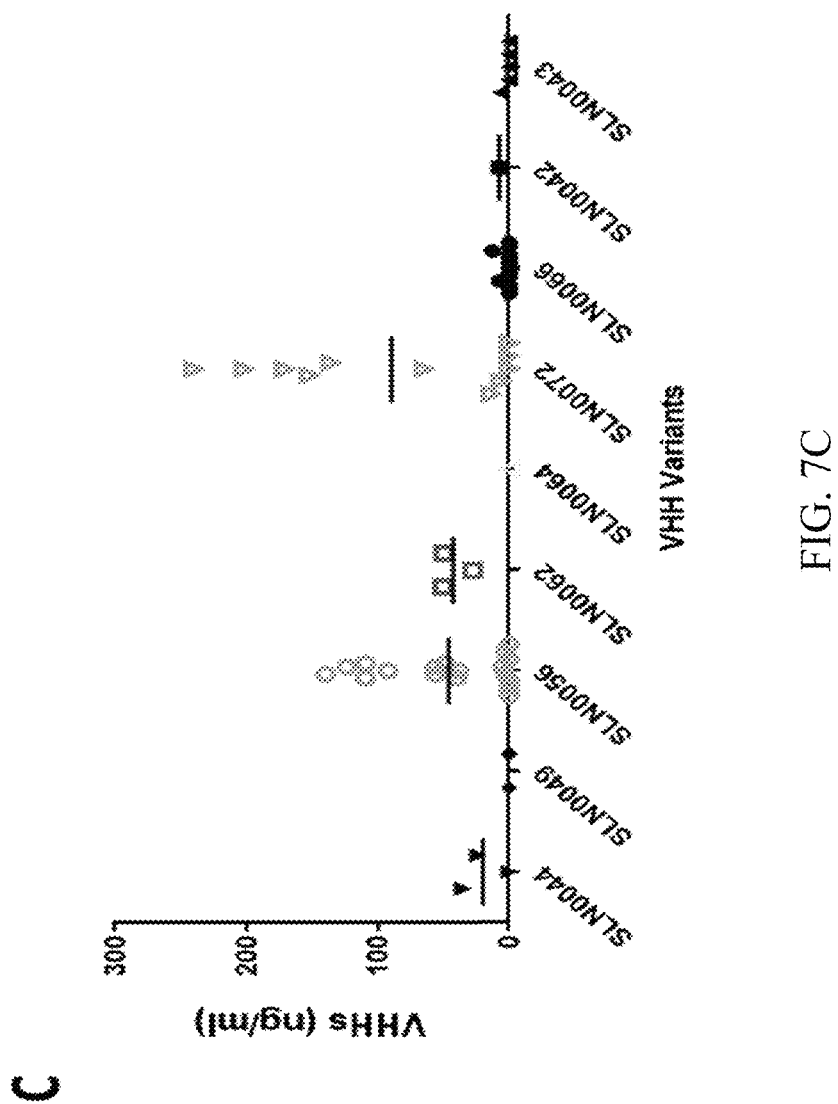
Figure 8A:
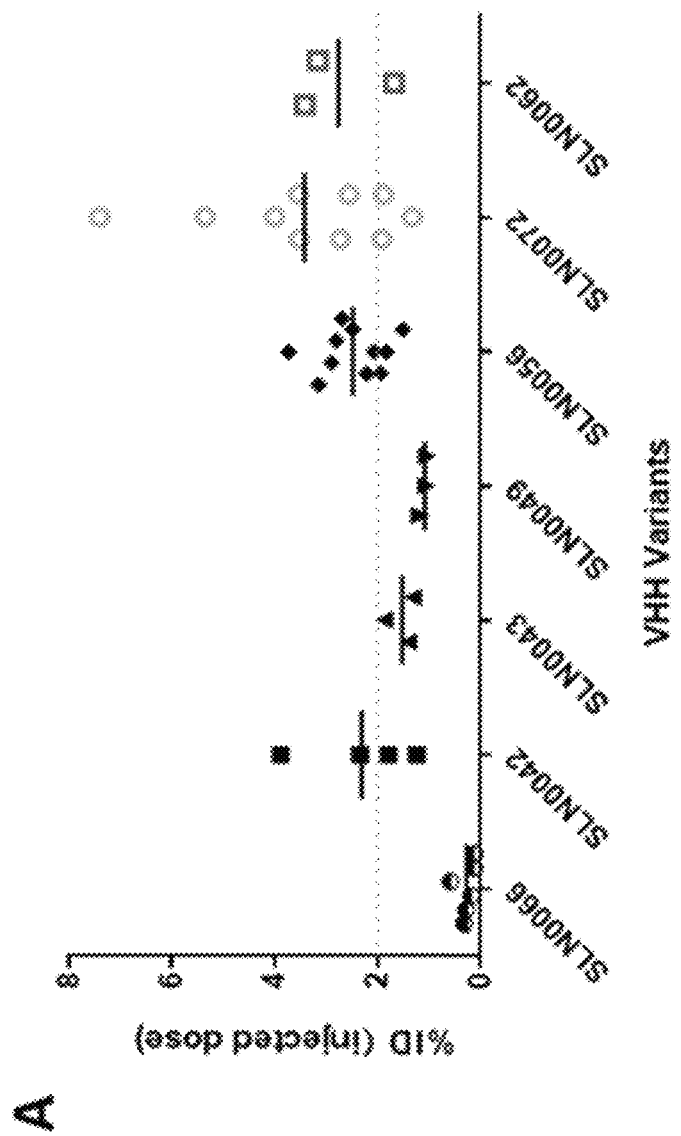
FIG. 8A-8B, 8Ca-f illustrates that the transferrin binding protein enabled the associated OVA to cross blood-brain barrier in mice, and dependency of such capabilities is associated with epitope utilization and affinity.
Figure 8B:
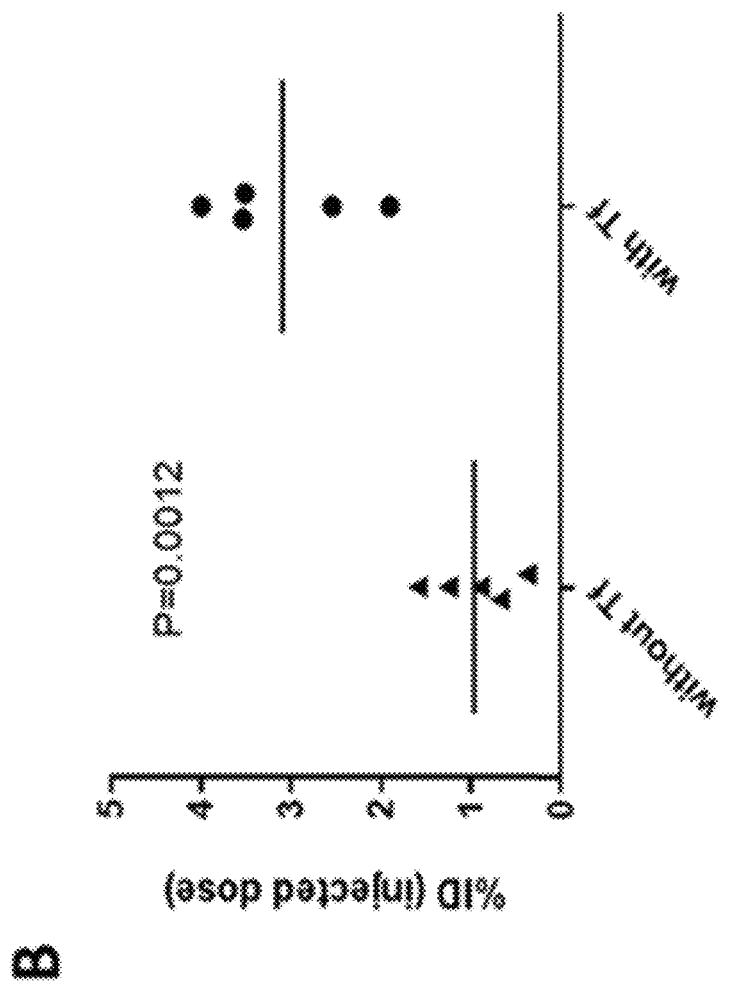
Figure 8C:
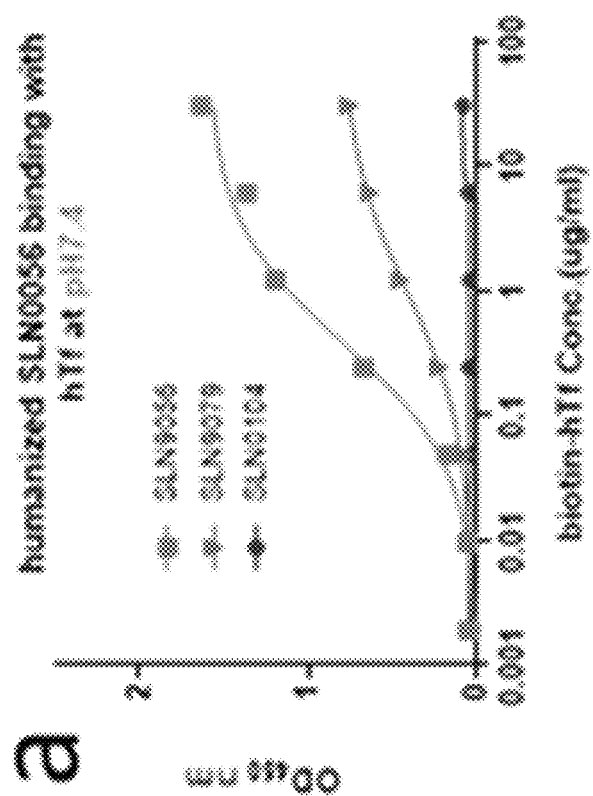
Figure 8C:
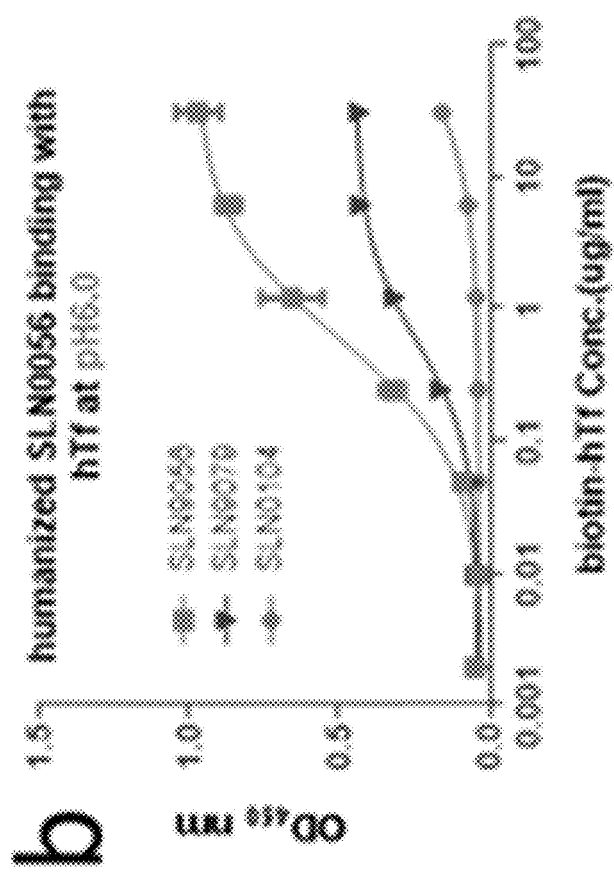
Figure 8C:
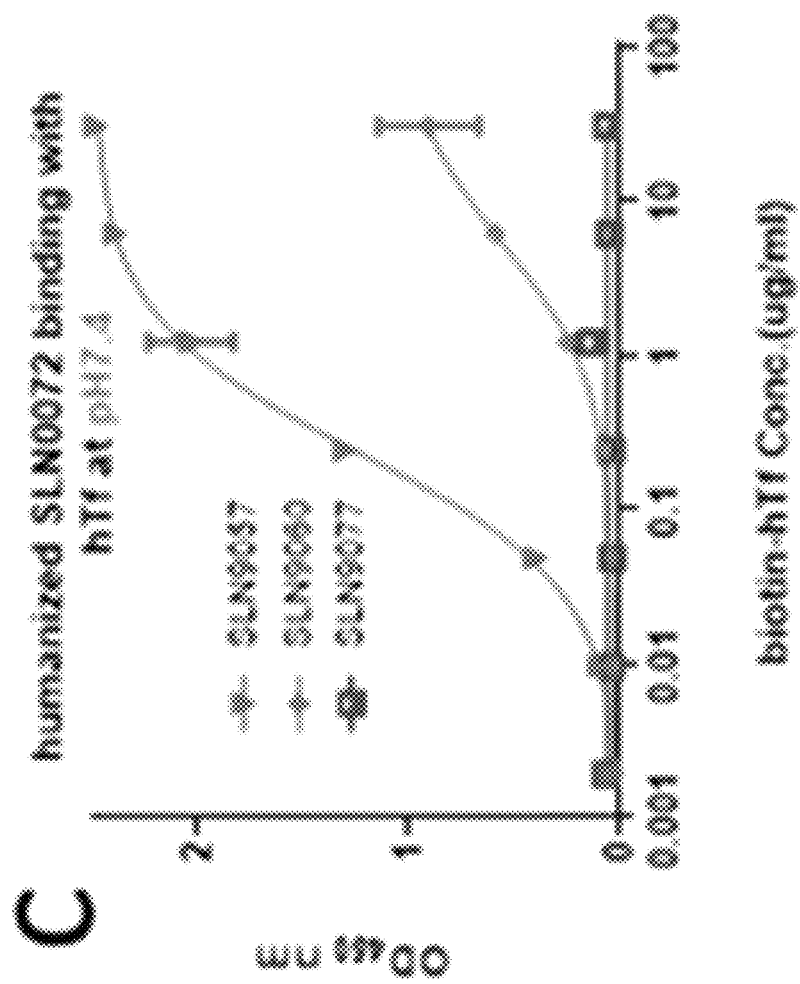
Figure 8C:
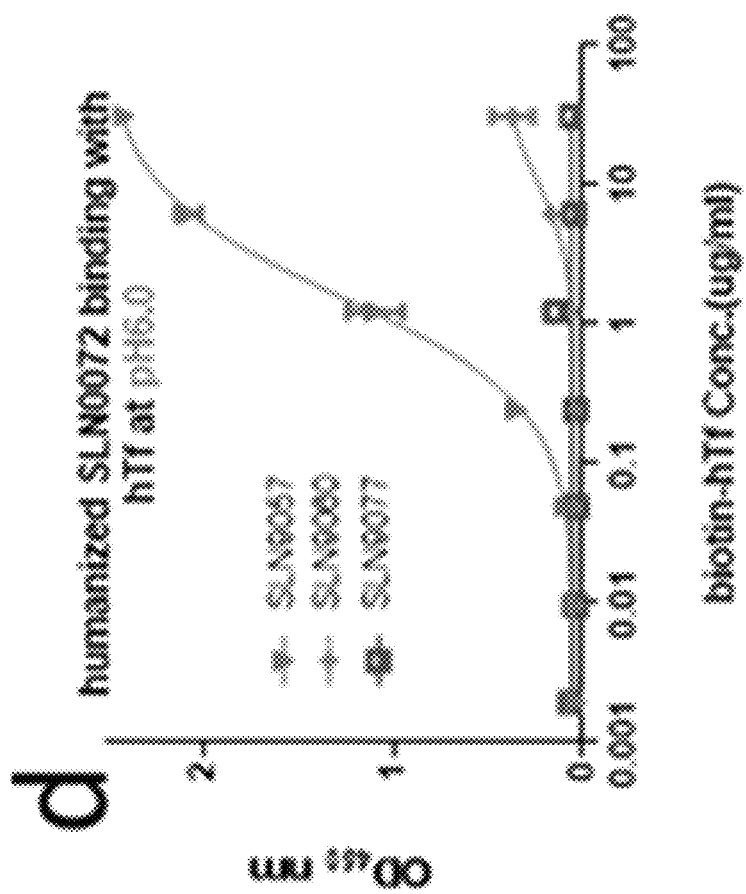
Figure 8C:
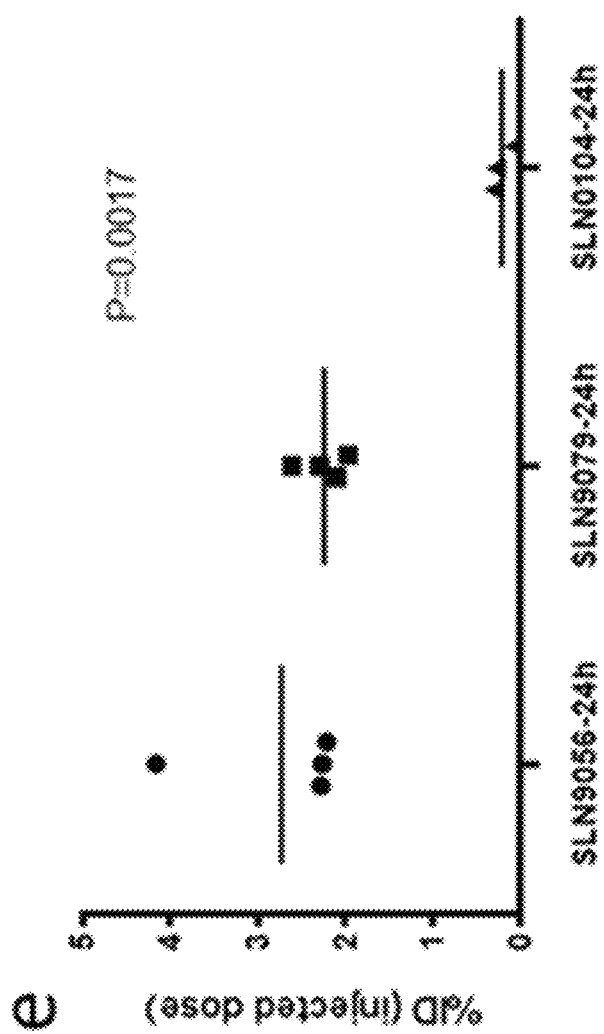
Figure 8F:
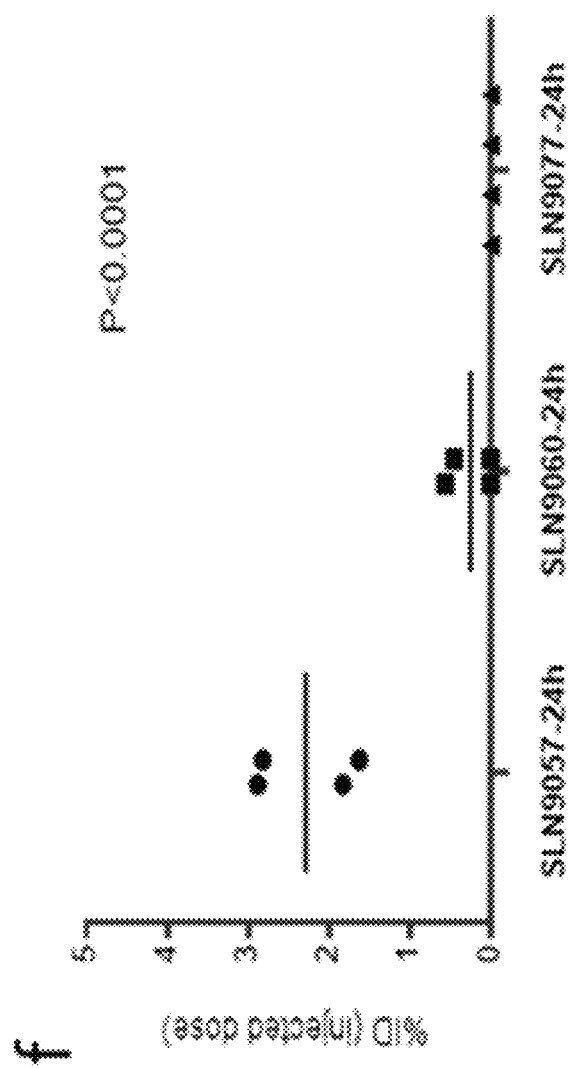

Data shown in FIG. 7 suggested that VHH's possess variable capabilities to cross the monolayer of Caco-2 cells, partially reflecting its affinity to human transferrin or epitope on transferrin for binding. The results also suggested essential roles of transferrin in the VHH-enabled transmembrane absorption of biological molecules through intestinal epithelium (FIG. 7B).

Humanization of the Selected VHH's

VHH's with the expected properties in enabling transmembrane translocation of the fused OVA protein, as well as with less risk factors for development, were selected for humanization. CDR residues within the selected VHH's were determined and annotated with Kabat numbering system. N-glycosylation site, and deamination site within the CDRs, N-glycosylation sites or cysteine within or close to CDR will be regarded as risk factors for future development. VHH humanization was conducted by following standard procedures of CDR grafting and structural refinement. Upon the humanization design, recombinant DNA constructs were created to produce recombinant VHH-OVA-His as described above for ELISA- and FACS-based binding assays. The humanized sequences with an affinity equal to or better than that of the original VHH to transferrin, while having acceptable expression and stability levels were selected for further development.

FIG. 5 indicated that the humanized VHH variants possess similar profile as the original VHH regarding its binding to transferrin.

Example 3 Using Tf-Binding VHH for Half-Life Extension of its Associated Entities Fusion proteins were produced with recombinant DNA technology by fusing the indicated protein at C- or N-terminus of VHH, with or without linkers. The proteins were purified to homogeneity, formulated in appropriate buffer, and quantitated with Bradford methods for use in in vivo tests. All animal procedures were reviewed and approved by institutional review board (IRB).

Mice of different genetic strains including C57BL/6, Balb/c and CR6 were grouped upon genetic background, gender and body weight. The test articles such as proteins fused to the transferrin-binding protein, as well as a negative control (a recombinant protein produced in a same way but containing a VHH that doses not bind to transferrin) were administered through IV or SC injection at a dosage of 3 mg/kg, with or without co-dosing of human transferrin (5 mg/kg). For the groups in which transferrin was co-dosed, daily dosing of human transferrin at 5 mg/kg were continued for 10 days.

To determine serum half-life of the test articles in mice, 40 μL of whole blood was collected from the subcutaneous vein of the outer corner of the eye at multiple time points. Serum was recovered by centrifugation at 10000 rpm for 10 min after the collected whole blood was placed at room temperature for 1 hour, concentrations of VHH-fused proteins within serum were measured by quantitative ELISA. For OVA-VHH-His or GLP-1-VHH-His proteins, rabbit anti-OVA polyclonal antibodies (Sigma C6534-2 mL) or a monoclonal anti-GLP-1 antibody, respectively, was paired with a biotinylated rabbit anti-VHH antibody (GeneScript, A02015-200) for specific and quantitative measurement, referring a standard curve developed with the purified recombinant protein by using a protocol as qualified with inter-assay CV's less than 20% and recovery rate more than 90%. PK parameters were calculated by PKsovler software.

Results shown as in FIG. 6 indicated the transferrin-binding VHH enabled extension of the serum half-life of its associated OVA as well as GLP-1, and such effect was dependent on affinity of the VHH to transferrin and epitope utilized for binding.

Example 4 Transferrin-Binding VHH Enabled Oral Delivery of the Associated Entities As in half-life studies, grouped mice were put under anesthesia by using 250 mg/kg tribromoethanol, then the abdominal hair of mice was shaved and disinfected with the iodine and alcohol. The skin of the middle abdomen was cut at a length of about 0.5-1 cm by surgical scissors to expose the duodenum for injection of the test articles or a control (the purified VHH-OVA-His protein) with or without mixture of transferrin and $Fe^{3+}$. Wound was sutured with iodine disinfection. Alternatively, the test articles or control were administered through intragastric injection by inserting gavage needle into the mouse stomach. After the oral dosing, blood samples were collected at multiple time point to recover serum as described above. Concentrations of VHH-fused proteins were quantitated by following procedure described in Example 3.

Data shown in FIG. 7 indicated that the transferrin-binding VHH enabled the orally dosed VHH-OVA fusion proteins to cross intestinal epithelium and be absorbed to blood stream, and therefore demonstrated potentials in delivering therapeutic biologics through oral dosing route.

Example 5 Transferrin-Binding VHHs Enabled the Associated Entities to Cross Blood-Brain Barrier As in the half-life studies, mice were dosed with the purified recombinant proteins (e.g. VHH-OVA-His) at 10 mg/kg by IV injection, with or without 10 mg/kg of human transferrin by IP injection. At multiple time points post dosing, brains were collected and frozen in liquid nitrogen after perfusion with 20 mL of PBS. Proteins were extracted by following standard procedures for ELISA-based quantitative measurement. One quantitative ELISA format was using labbit-anti-OVA polyclonal antibody (Sigma C6534-2 mL) for coating and biotinylated rabbit anti-VHH antibodies (GeneScript, A02015-200) for detection. Data shown in FIG. 8 indicated that, compared to the negative control (SLN0066, one VHH that does not bind to transferrin, SEQ ID NO: 110), the test articles (VHH's that demonstrated binding capabilities to transferrin) significantly elevated the levels of the test articles within brain tissue (regarding mean % ID or percentage of injection dosage, ~1.03% to ~3.5% at 24 h after administration for the selected VHH's). the data also clearly indicated the VHH-enabled crossing BBB was associated to transferrin (groups co-dosed with transferrin had ~3.2-fold higher % ID than that of the group treated with VHH-OVA-His only).

By using the humanized VHH variants that share same CDR's (and thus supposedly bind to the same epitope on transferrin) but with different affinities, impact of the VHH's affinity to transferrin on the capabilities to mediate the BBB-crossing was also determined. The data in FIG. 8C further supported the conclusion on dependency of transferrin binding of the VHH-enabled BBB-crossing capabilities, but also clearly suggested a relationship between VHH's affinity to transferrin and its capability to mediate the BBB-crossing. Higher BBB-crossing was observed with the VHH variants that possess the higher affinity to transferrin.

Example 6 Transferrin-Binding VHH's Enabled Intracellular Delivery of its Associated Entities Levels of transferrin receptors are also elevated on the membrane surface of multiple types of cells, for example tumor cells. Therefore, the transferrin-binding VHH's would be favorable for targeted drug delivery especially intracellular delivery to tumor cells. To test such hypothesis, recombinant VHH-PE38-His proteins were produced in E. coli and purified to homogeneity. Efficacy of intracellular delivery was tested on monolayer culture of Hepa-G2 cells (constitutively expressing TfR) and MDCK cells (with or without heterotopic TfR1 expression from transfected recombinant plasmid). Briefly, cells were seeded at a desired density into 96-well microplates within 100 µL of culture medium and cultured at 37° C. overnight. After cells were washed with fresh pre-warmed medium, serially diluted VHH-PE38-His with or without human transferrin prepared in culture medium were added to the cell culture. At multiple time points post the treatment, live cells were quantitated with CellTiter-Glo® Reagent as instructed by the manufacturer's manual. Luminescence signals were recorded at an integration time of 0.25-1 second per well and data were analyzed with GraphPad.

Figure 9A:
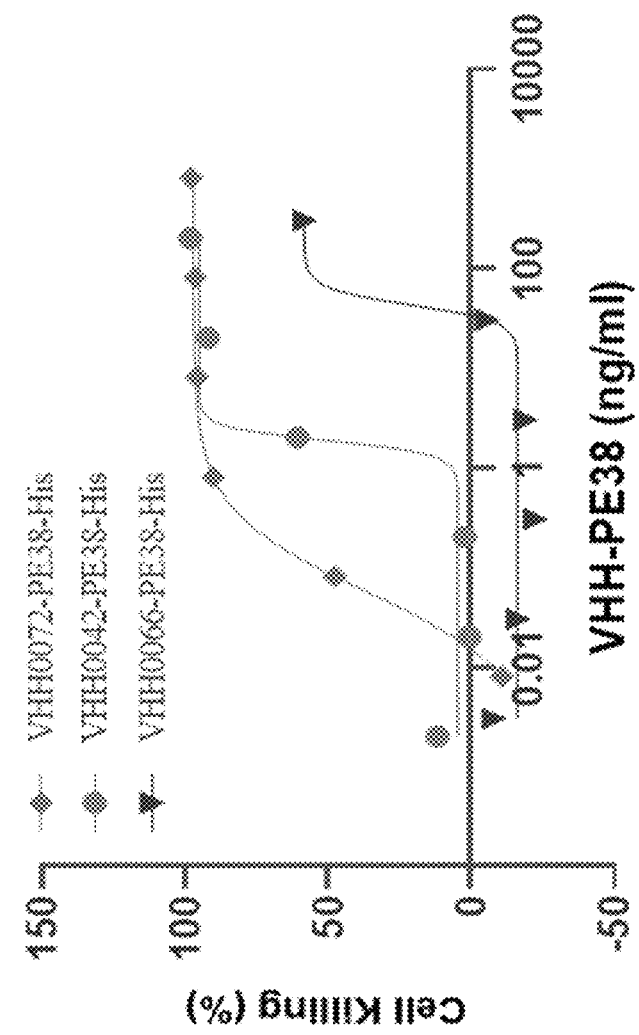
Figure 9B:
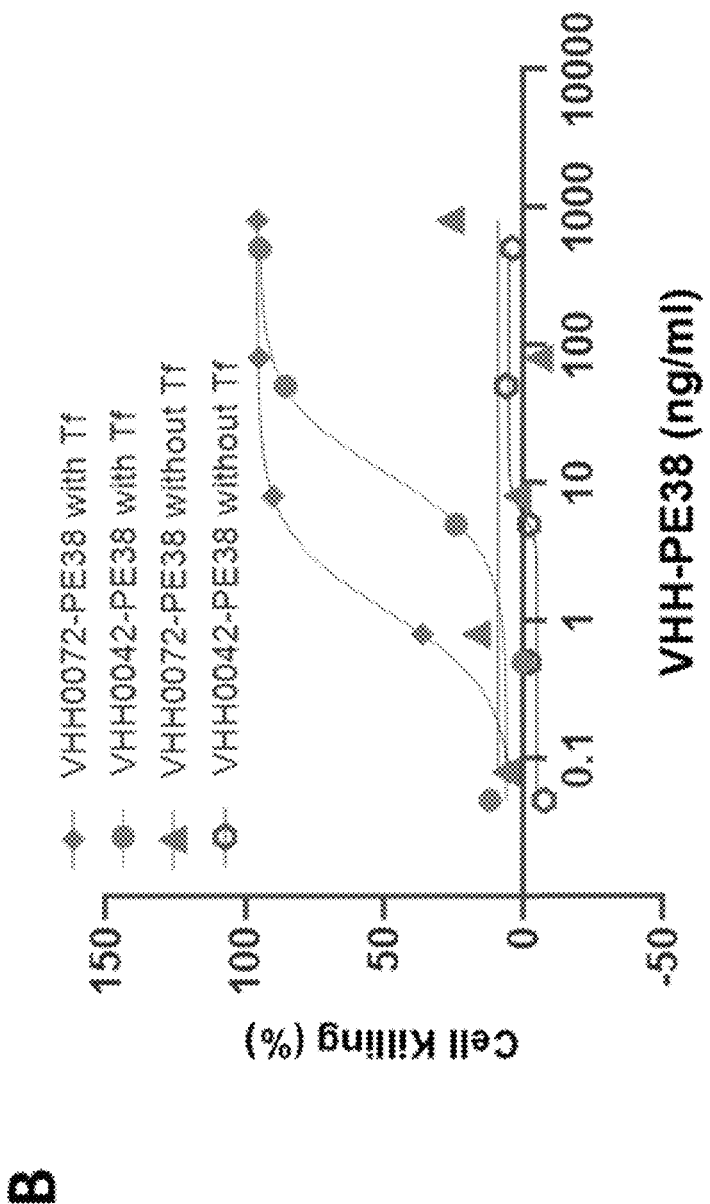

Data shown in FIG. 9 indicated that the transferrin-binding VHH's enabled intracellular delivery of the associated entities into cells that express transferrin receptor(s) on surface, and such capabilities were dependent on transferrin-binding activity of the VHH's. VHH's with different epitope utilization (belonging to different bins or having different CDR sequences) demonstrated differential efficacy in intracellular delivery as well.

Figure 10:
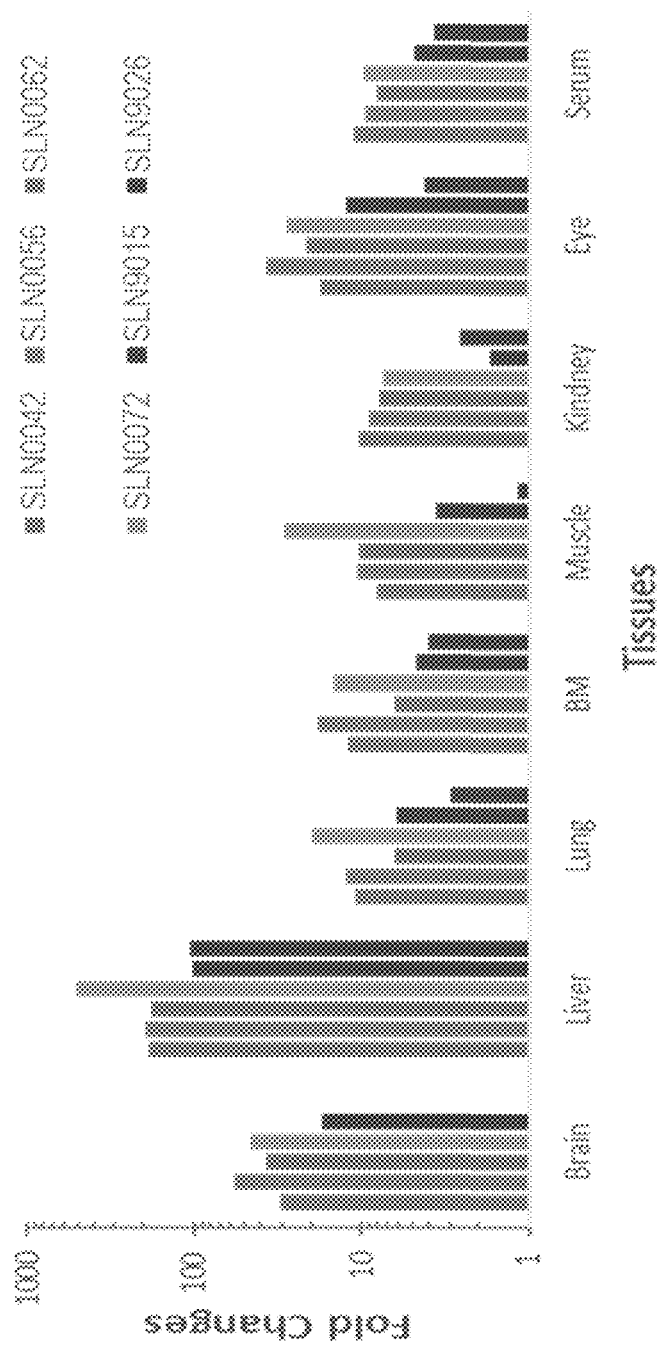
FIG. 10 illustrates the biodistribution of the transferrin binding protein variants after systemic administration.

Example 7 the Transferrin-Binding VHH's Enabled Organ or Tissue-Targeted Delivery of the Associated Entities Biodistribution of the iv administered recombinant proteins (e.g VHH-OVA-His) was also investigated in mice with different genetic background. At multiple time points post iv injection, samples were collected from liver, lung, bone marrow, heart, muscle and blood et al. after blood vessels were perfused with 30 mL of PBS. Samples were weighted and homogenized to extract soluble proteins for quantitative ELISA-based measurement as described above. Referring to a standard curve developed with the purified recombinant proteins, the data were normalized upon tissue weights or volumes. Biodistribution of the VHH-OVA-His proteins was analyzed upon fold-changes compared to the control VHH that does not bind to transferrin. Data shown in FIG. 10 indicated the selected transferrin-binding VHH's enabled targeted delivery to liver, brain, bone marrow, lung, muscle, kidney, eyes and other organs or tissues which express transferrin receptor(s). The transferrin-binding VHH's in this invention may have potential applications for drug delivery targeting different tissues, especially for brain, liver and bone marrow.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

SEQUENCE LISTING

```
Sequence total quantity: 110
SEQ ID NO: 1              moltype = AA  length = 5
FEATURE                   Location/Qualifiers
REGION                    1..5
                          note =
                          SLN9056/SLN0056/SLN9015/SLN9079/SLN0104/SLN0100/SLN0097
                           HCDR1
source                    1..5
                          mol_type = protein
                          organism = synthetic construct
SEQUENCE: 1
GNYMG                                                                    5

SEQ ID NO: 2              moltype = AA  length = 5
FEATURE                   Location/Qualifiers
REGION                    1..5
                          note =
                          SLN9057/SLN0072/SLN9060/SLN9061/SLN9062/SLN9077/SLN9058/SLN
                          0105 HCDR1
source                    1..5
                          mol_type = protein
                          organism = synthetic construct
SEQUENCE: 2
SSYMG                                                                    5

SEQ ID NO: 3              moltype = AA  length = 6
FEATURE                   Location/Qualifiers
REGION                    1..6
                          note = SLN0042 HCDR1
source                    1..6
                          mol_type = protein
                          organism = synthetic construct
SEQUENCE: 3
SFTCMG                                                                   6

SEQ ID NO: 4              moltype = AA  length = 5
FEATURE                   Location/Qualifiers
REGION                    1..5
                          note = SLN0043 HCDR1
source                    1..5
                          mol_type = protein
                          organism = synthetic construct
SEQUENCE: 4
RDWMA                                                                    5

SEQ ID NO: 5              moltype = AA  length = 5
FEATURE                   Location/Qualifiers
REGION                    1..5
                          note = SLN0044 HCDR1
source                    1..5
                          mol_type = protein
                          organism = synthetic construct
SEQUENCE: 5
TACMA                                                                    5

SEQ ID NO: 6              moltype = AA  length = 5
FEATURE                   Location/Qualifiers
REGION                    1..5
                          note = SLN0045/SLN0046 HCDR1
source                    1..5
                          mol_type = protein
                          organism = synthetic construct
SEQUENCE: 6
RACMA                                                                    5

SEQ ID NO: 7              moltype = AA  length = 5
FEATURE                   Location/Qualifiers
REGION                    1..5
                          note = SLN0049 HCDR1
source                    1..5
                          mol_type = protein
                          organism = synthetic construct
SEQUENCE: 7
RYSMG                                                                    5

SEQ ID NO: 8              moltype = AA  length = 5
FEATURE                   Location/Qualifiers
REGION                    1..5
```

```
                          note = SLN0057 HCDR1
source                    1..5
                          mol_type = protein
                          organism = synthetic construct
SEQUENCE: 8
IYYMA                                                                    5

SEQ ID NO: 9              moltype = AA  length = 5
FEATURE                   Location/Qualifiers
REGION                    1..5
                          note = SLN0059/SLN9014 HCDR1
source                    1..5
                          mol_type = protein
                          organism = synthetic construct
SEQUENCE: 9
NYYMT                                                                    5

SEQ ID NO: 10             moltype = AA  length = 5
FEATURE                   Location/Qualifiers
REGION                    1..5
                          note = SLN0062 HCDR1
source                    1..5
                          mol_type = protein
                          organism = synthetic construct
SEQUENCE: 10
RNCMG                                                                    5

SEQ ID NO: 11             moltype = AA  length = 5
FEATURE                   Location/Qualifiers
REGION                    1..5
                          note = SLN0064 HCDR1
source                    1..5
                          mol_type = protein
                          organism = synthetic construct
SEQUENCE: 11
WFCMG                                                                    5

SEQ ID NO: 12             moltype = AA  length = 5
FEATURE                   Location/Qualifiers
REGION                    1..5
                          note = SLN0065 HCDR1
source                    1..5
                          mol_type = protein
                          organism = synthetic construct
SEQUENCE: 12
LFWMG                                                                    5

SEQ ID NO: 13             moltype = AA  length = 5
FEATURE                   Location/Qualifiers
REGION                    1..5
                          note = SLN0071 HCDR1
source                    1..5
                          mol_type = protein
                          organism = synthetic construct
SEQUENCE: 13
RCCMG                                                                    5

SEQ ID NO: 14             moltype = AA  length = 5
FEATURE                   Location/Qualifiers
REGION                    1..5
                          note = SLN0058 HCDR1
source                    1..5
                          mol_type = protein
                          organism = synthetic construct
SEQUENCE: 14
SDCMG                                                                    5

SEQ ID NO: 15             moltype = AA  length = 5
FEATURE                   Location/Qualifiers
REGION                    1..5
                          note = SLN9008 HCDR1
source                    1..5
                          mol_type = protein
                          organism = synthetic construct
SEQUENCE: 15
GHCMA                                                                    5

SEQ ID NO: 16             moltype = AA  length = 5
FEATURE                   Location/Qualifiers
```

```
REGION                  1..5
                        note = SLN9013 HCDR1
source                  1..5
                        mol_type = protein
                        organism = synthetic construct
SEQUENCE: 16
RGCMG                                                                       5

SEQ ID NO: 17           moltype = AA  length = 5
FEATURE                 Location/Qualifiers
REGION                  1..5
                        note = SLN9025 HCDR1
source                  1..5
                        mol_type = protein
                        organism = synthetic construct
SEQUENCE: 17
QHCMG                                                                       5

SEQ ID NO: 18           moltype = AA  length = 5
FEATURE                 Location/Qualifiers
REGION                  1..5
                        note = SLN9026 HCDR1
source                  1..5
                        mol_type = protein
                        organism = synthetic construct
SEQUENCE: 18
SKCMA                                                                       5

SEQ ID NO: 19           moltype = AA  length = 5
FEATURE                 Location/Qualifiers
REGION                  1..5
                        note = 1902-2-1-mm-F7 HCDR1
source                  1..5
                        mol_type = protein
                        organism = synthetic construct
SEQUENCE: 19
RACMG                                                                       5

SEQ ID NO: 20           moltype = AA  length = 5
FEATURE                 Location/Qualifiers
REGION                  1..5
                        note = 1902-2-1-hh-B12 HCDR1
source                  1..5
                        mol_type = protein
                        organism = synthetic construct
SEQUENCE: 20
KYCMG                                                                       5

SEQ ID NO: 21           moltype = AA  length = 5
FEATURE                 Location/Qualifiers
REGION                  1..5
                        note = 1902-2-1-hm-D12 HCDR1
source                  1..5
                        mol_type = protein
                        organism = synthetic construct
SEQUENCE: 21
NYCMA                                                                       5

SEQ ID NO: 22           moltype = AA  length = 17
FEATURE                 Location/Qualifiers
REGION                  1..17
                        note =
                        SLN9056/SLN0056/SLN9015/SLN9079/SLN0104/SLN0100/SLN0097
                        HCDR2
source                  1..17
                        mol_type = protein
                        organism = synthetic construct
SEQUENCE: 22
VLYTGGGSTY YADSVKG                                                         17

SEQ ID NO: 23           moltype = AA  length = 17
FEATURE                 Location/Qualifiers
REGION                  1..17
                        note = SLN9057/SLN0072/SLN9062/SLN9077/SLN9058/SLN0105 HCDR2
source                  1..17
                        mol_type = protein
                        organism = synthetic construct
SEQUENCE: 23
QINSRSGSTY YADSVKG                                                         17
```

| | | |
|---|---|---|
| SEQ ID NO: 24<br>FEATURE<br>REGION<br><br>source | moltype = AA  length = 17<br>Location/Qualifiers<br>1..17<br>note = SLN0042 HCDR2<br>1..17<br>mol_type = protein<br>organism = synthetic construct | |
| SEQUENCE: 24<br>TINPGTGSTY YADSVKG | | 17 |
| SEQ ID NO: 25<br>FEATURE<br>REGION<br><br>source | moltype = AA  length = 17<br>Location/Qualifiers<br>1..17<br>note = SLN0043 HCDR2<br>1..17<br>mol_type = protein<br>organism = synthetic construct | |
| SEQUENCE: 25<br>AFVPSIGSTF YVDSVKG | | 17 |
| SEQ ID NO: 26<br>FEATURE<br>REGION<br><br>source | moltype = AA  length = 16<br>Location/Qualifiers<br>1..16<br>note = SLN0044 HCDR2<br>1..16<br>mol_type = protein<br>organism = synthetic construct | |
| SEQUENCE: 26<br>AIARYGDTTY TDSVKG | | 16 |
| SEQ ID NO: 27<br>FEATURE<br>REGION<br><br>source | moltype = AA  length = 16<br>Location/Qualifiers<br>1..16<br>note = SLN0045/SLN0046 HCDR2<br>1..16<br>mol_type = protein<br>organism = synthetic construct | |
| SEQUENCE: 27<br>WIIADGSTGY ADSVKG | | 16 |
| SEQ ID NO: 28<br>FEATURE<br>REGION<br><br>source | moltype = AA  length = 16<br>Location/Qualifiers<br>1..16<br>note = SLN0049 HCDR2<br>1..16<br>mol_type = protein<br>organism = synthetic construct | |
| SEQUENCE: 28<br>AIDSIGRTSY ADSVKG | | 16 |
| SEQ ID NO: 29<br>FEATURE<br>REGION<br><br>source | moltype = AA  length = 16<br>Location/Qualifiers<br>1..16<br>note = SLN0057 HCDR2<br>1..16<br>mol_type = protein<br>organism = synthetic construct | |
| SEQUENCE: 29<br>VIYRGGSTTY ADSAKG | | 16 |
| SEQ ID NO: 30<br>FEATURE<br>REGION<br><br>source | moltype = AA  length = 16<br>Location/Qualifiers<br>1..16<br>note = SLN0059 HCDR2<br>1..16<br>mol_type = protein<br>organism = synthetic construct | |
| SEQUENCE: 30<br>GLTRADVTLY ADSVKG | | 16 |
| SEQ ID NO: 31<br>FEATURE<br>REGION<br><br>source | moltype = AA  length = 17<br>Location/Qualifiers<br>1..17<br>note = SLN0062 HCDR2<br>1..17<br>mol_type = protein<br>organism = synthetic construct | |
| SEQUENCE: 31 | | |

```
TVYPGGGSTY YADSVKG                                                          17

SEQ ID NO: 32           moltype = AA  length = 16
FEATURE                 Location/Qualifiers
REGION                  1..16
                        note = SLN0064 HCDR2
source                  1..16
                        mol_type = protein
                        organism = synthetic construct
SEQUENCE: 32
VIDVDSIARY GDSVKG                                                           16

SEQ ID NO: 33           moltype = AA  length = 16
FEATURE                 Location/Qualifiers
REGION                  1..16
                        note = SLN0065 HCDR2
source                  1..16
                        mol_type = protein
                        organism = synthetic construct
SEQUENCE: 33
VTGRDGSTIY ADSVQG                                                           16

SEQ ID NO: 34           moltype = AA  length = 16
FEATURE                 Location/Qualifiers
REGION                  1..16
                        note = SLN0071 HCDR2
source                  1..16
                        mol_type = protein
                        organism = synthetic construct
SEQUENCE: 34
SINVLGGTSY ADSVKG                                                           16

SEQ ID NO: 35           moltype = AA  length = 17
FEATURE                 Location/Qualifiers
REGION                  1..17
                        note = SLN0058 HCDR2
source                  1..17
                        mol_type = protein
                        organism = synthetic construct
SEQUENCE: 35
TIATAGGSTG YADSVKG                                                          17

SEQ ID NO: 36           moltype = AA  length = 18
FEATURE                 Location/Qualifiers
REGION                  1..18
                        note = SLN9008 HCDR2
source                  1..18
                        mol_type = protein
                        organism = synthetic construct
SEQUENCE: 36
AIYTGTGSTY YADESVKG                                                         18

SEQ ID NO: 37           moltype = AA  length = 17
FEATURE                 Location/Qualifiers
REGION                  1..17
                        note = SLN9013 HCDR2
source                  1..17
                        mol_type = protein
                        organism = synthetic construct
SEQUENCE: 37
SFLHGAASAD YADSVKG                                                          17

SEQ ID NO: 38           moltype = AA  length = 17
FEATURE                 Location/Qualifiers
REGION                  1..17
                        note = SLN9025 HCDR2
source                  1..17
                        mol_type = protein
                        organism = synthetic construct
SEQUENCE: 38
YTYVSFNVTH YADSVKG                                                          17

SEQ ID NO: 39           moltype = AA  length = 17
FEATURE                 Location/Qualifiers
REGION                  1..17
                        note = SLN9026 HCDR2
source                  1..17
                        mol_type = protein
                        organism = synthetic construct
```

```
                                              -continued
SEQUENCE: 39
AIDTSRGRAY LTDSVKG                                                              17

SEQ ID NO: 40          moltype = AA  length = 17
FEATURE                Location/Qualifiers
REGION                 1..17
                       note = SLN9060 HCDR2
source                 1..17
                       mol_type = protein
                       organism = synthetic construct
SEQUENCE: 40
QIQSRSGSTY YADSVKG                                                              17

SEQ ID NO: 41          moltype = AA  length = 17
FEATURE                Location/Qualifiers
REGION                 1..17
                       note = SLN9061 HCDR2
source                 1..17
                       mol_type = protein
                       organism = synthetic construct
SEQUENCE: 41
QINARSGSTY YADSVKG                                                              17

SEQ ID NO: 42          moltype = AA  length = 17
FEATURE                Location/Qualifiers
REGION                 1..17
                       note = 1902-2-1-mm-F7 HCDR2
source                 1..17
                       mol_type = protein
                       organism = synthetic construct
SEQUENCE: 42
RVYSDGSQSY YPDSVKG                                                              17

SEQ ID NO: 43          moltype = AA  length = 16
FEATURE                Location/Qualifiers
REGION                 1..16
                       note = 1902-2-1-hh-B12 HCDR2
source                 1..16
                       mol_type = protein
                       organism = synthetic construct
SEQUENCE: 43
AIDSDGTTRY ADSVQG                                                               16

SEQ ID NO: 44          moltype = AA  length = 16
FEATURE                Location/Qualifiers
REGION                 1..16
                       note = 1902-2-1-hm-D12 HCDR2
source                 1..16
                       mol_type = protein
                       organism = synthetic construct
SEQUENCE: 44
NMNSYDWTDY DDSVKG                                                               16

SEQ ID NO: 45          moltype = AA  length = 19
FEATURE                Location/Qualifiers
REGION                 1..19
                       note = SLN9056/SLN0056/SLN9079/SLN0104/SLN0100/SLN0097 HCDR3
source                 1..19
                       mol_type = protein
                       organism = synthetic construct
SEQUENCE: 45
ALGSARWYTS SLDARAYNI                                                            19

SEQ ID NO: 46          moltype = AA  length = 18
FEATURE                Location/Qualifiers
REGION                 1..18
                       note = SLN9057 HCDR3
source                 1..18
                       mol_type = protein
                       organism = synthetic construct
SEQUENCE: 46
RFGPTFYAIN LGSNLYNY                                                             18

SEQ ID NO: 47          moltype = AA  length = 16
FEATURE                Location/Qualifiers
REGION                 1..16
                       note = SLN0042 HCDR3
source                 1..16
                       mol_type = protein
```

-continued

```
SEQUENCE: 47
TQLFGCGSLA KSLFGY                                                   16

SEQ ID NO: 48           moltype = AA  length = 20
FEATURE                 Location/Qualifiers
REGION                  1..20
                        note = SLN0043 HCDR3
source                  1..20
                        mol_type = protein
                        organism = synthetic construct
SEQUENCE: 48
DPLWGRKYGG SWSDPSEYNY                                               20

SEQ ID NO: 49           moltype = AA  length = 15
FEATURE                 Location/Qualifiers
REGION                  1..15
                        note = SLN0044 HCDR3
source                  1..15
                        mol_type = protein
                        organism = synthetic construct
SEQUENCE: 49
KSPNSGCDEY AHYET                                                    15

SEQ ID NO: 50           moltype = AA  length = 17
FEATURE                 Location/Qualifiers
REGION                  1..17
                        note = SLN0045 HCDR3
source                  1..17
                        mol_type = protein
                        organism = synthetic construct
SEQUENCE: 50
AYNGGDRCYT LIGLYNH                                                  17

SEQ ID NO: 51           moltype = AA  length = 16
FEATURE                 Location/Qualifiers
REGION                  1..16
                        note = SLN0049 HCDR3
source                  1..16
                        mol_type = protein
                        organism = synthetic construct
SEQUENCE: 51
TAWRDWATLR EYEYGY                                                   16

SEQ ID NO: 52           moltype = AA  length = 16
FEATURE                 Location/Qualifiers
REGION                  1..16
                        note = SLN0057 HCDR3
source                  1..16
                        mol_type = protein
                        organism = synthetic construct
SEQUENCE: 52
AHVLHVSSLL PGGYPY                                                   16

SEQ ID NO: 53           moltype = AA  length = 15
FEATURE                 Location/Qualifiers
REGION                  1..15
                        note = SLN0059 HCDR3
source                  1..15
                        mol_type = protein
                        organism = synthetic construct
SEQUENCE: 53
ADRFRVGLRE ADFSA                                                    15

SEQ ID NO: 54           moltype = AA  length = 16
FEATURE                 Location/Qualifiers
REGION                  1..16
                        note = SLN0062 HCDR3
source                  1..16
                        mol_type = protein
                        organism = synthetic construct
SEQUENCE: 54
SRRIWSCGSG AGSYDY                                                   16

SEQ ID NO: 55           moltype = AA  length = 20
FEATURE                 Location/Qualifiers
REGION                  1..20
                        note = SLN0064 HCDR3
source                  1..20
```

```
                            mol_type = protein
                            organism = synthetic construct
SEQUENCE: 55
KTERQCRWNW MDWRTYDYPH                                                   20

SEQ ID NO: 56               moltype = AA   length = 18
FEATURE                     Location/Qualifiers
REGION                      1..18
                            note = SLN0065 HCDR3
source                      1..18
                            mol_type = protein
                            organism = synthetic construct
SEQUENCE: 56
DQTRYSSLRL LAPNRSAS                                                     18

SEQ ID NO: 57               moltype = AA   length = 19
FEATURE                     Location/Qualifiers
REGION                      1..19
                            note = SLN0071 HCDR3
source                      1..19
                            mol_type = protein
                            organism = synthetic construct
SEQUENCE: 57
GLASAPWRPC GTTTEEYKY                                                    19

SEQ ID NO: 58               moltype = AA   length = 18
FEATURE                     Location/Qualifiers
REGION                      1..18
                            note = SLN0072/SLN9060/SLN9061/SLN9062/SLN9058/SLN0105 HCDR3
source                      1..18
                            mol_type = protein
                            organism = synthetic construct
SEQUENCE: 58
RFGPTFYPVP LGSNLYNY                                                     18

SEQ ID NO: 59               moltype = AA   length = 16
FEATURE                     Location/Qualifiers
REGION                      1..16
                            note = SLN0046 HCDR3
source                      1..16
                            mol_type = protein
                            organism = synthetic construct
SEQUENCE: 59
YNGGDRCYTL IGLYNH                                                       16

SEQ ID NO: 60               moltype = AA   length = 18
FEATURE                     Location/Qualifiers
REGION                      1..18
                            note = SLN0058 HCDR3
source                      1..18
                            mol_type = protein
                            organism = synthetic construct
SEQUENCE: 60
WGGAWWYPWC EFVFSNGY                                                     18

SEQ ID NO: 61               moltype = AA   length = 16
FEATURE                     Location/Qualifiers
REGION                      1..16
                            note = SLN9008 HCDR3
source                      1..16
                            mol_type = protein
                            organism = synthetic construct
SEQUENCE: 61
TLLYGCGAWS PRLFGY                                                       16

SEQ ID NO: 62               moltype = AA   length = 19
FEATURE                     Location/Qualifiers
REGION                      1..19
                            note = SLN9013 HCDR3
source                      1..19
                            mol_type = protein
                            organism = synthetic construct
SEQUENCE: 62
NPVVASCHYR LRSKYAYNY                                                    19

SEQ ID NO: 63               moltype = AA   length = 19
FEATURE                     Location/Qualifiers
REGION                      1..19
                            note = SLN9015 HCDR3
```

```
source                    1..19
                          mol_type = protein
                          organism = synthetic construct
SEQUENCE: 63
VLGSARWYTS SLDARAYNI                                                    19

SEQ ID NO: 64             moltype = AA   length = 14
FEATURE                   Location/Qualifiers
REGION                    1..14
                          note = SLN9025 HCDR3
source                    1..14
                          mol_type = protein
                          organism = synthetic construct
SEQUENCE: 64
GYYSCGVSTT GYNY                                                         14

SEQ ID NO: 65             moltype = AA   length = 21
FEATURE                   Location/Qualifiers
REGION                    1..21
                          note = SLN9026 HCDR3
source                    1..21
                          mol_type = protein
                          organism = synthetic construct
SEQUENCE: 65
SNTFYNCGAL NLGIGAGLVA Y                                                 21

SEQ ID NO: 66             moltype = AA   length = 18
FEATURE                   Location/Qualifiers
REGION                    1..18
                          note = SLN9077 HCDR3
source                    1..18
                          mol_type = protein
                          organism = synthetic construct
SEQUENCE: 66
RFGPTFYTGN LGSNLYNY                                                     18

SEQ ID NO: 67             moltype = AA   length = 20
FEATURE                   Location/Qualifiers
REGION                    1..20
                          note = 1902-2-1-mm-F7 HCDR3
source                    1..20
                          mol_type = protein
                          organism = synthetic construct
SEQUENCE: 67
LLMSDYYSCR VRFHQSDFRD                                                   20

SEQ ID NO: 68             moltype = AA   length = 20
FEATURE                   Location/Qualifiers
REGION                    1..20
                          note = 1902-2-1-hh-B12 HCDR3
source                    1..20
                          mol_type = protein
                          organism = synthetic construct
SEQUENCE: 68
DRWSMKYYSD YALFPGGYNY                                                   20

SEQ ID NO: 69             moltype = AA   length = 22
FEATURE                   Location/Qualifiers
REGION                    1..22
                          note = 1902-2-1-hm-D12 HCDR3
source                    1..22
                          mol_type = protein
                          organism = synthetic construct
SEQUENCE: 69
RDCALRYCTR SYCTREAHFF KY                                                22

SEQ ID NO: 70             moltype = AA   length = 128
FEATURE                   Location/Qualifiers
REGION                    1..128
                          note = SLN9056
source                    1..128
                          mol_type = protein
                          organism = synthetic construct
SEQUENCE: 70
EVQLVESGGG LVQPGGSLRL SCAASGHAYG GNYMGWFRQA PGKGLEGVAV LYTGGGSTYY        60
ADSVKGRFTI SEDNSKNTVY LQMNSLRAED TAVYYCALAL GSARWYTSSL DARAYNIWGQ       120
GTLVTVSS                                                               128

SEQ ID NO: 71             moltype = AA   length = 127
```

```
FEATURE              Location/Qualifiers
REGION               1..127
                     note = SLN9057
source               1..127
                     mol_type = protein
                     organism = synthetic construct
SEQUENCE: 71
EVQLVESGGG LVQPGGSLRL SCAASGYTGS SSYMGWFRQA PGKGLEGVSQ INSRSGSTYY    60
ADSVKGRFTI SRDNSKNTLY LQMNSLRAED TAVYYCAERF GPTFYAINLG SNLYNYWGQG   120
TLVTVSS                                                             127

SEQ ID NO: 72        moltype = AA  length = 125
FEATURE              Location/Qualifiers
REGION               1..125
                     note = SLN0042
source               1..125
                     mol_type = protein
                     organism = synthetic construct
SEQUENCE: 72
DVQLVESGGG SVQAGGSLRL SCAASGYTRS FTCMGWFRQA PGKEREGVAT INPGTGSTYY    60
ADSVKGRFSI SQDNAKNTVY LQMNTLKPED TAMYYCAATQ LFGCGSLAKS LFGYWGQGTL   120
VTVSS                                                               125

SEQ ID NO: 73        moltype = AA  length = 129
FEATURE              Location/Qualifiers
REGION               1..129
                     note = SLN0043
source               1..129
                     mol_type = protein
                     organism = synthetic construct
SEQUENCE: 73
DVQLVESGGG SVQAGGSLRL SCAASGYTWS RDWMAWFRQA PGKEREGVAA FVPSIGSTFY    60
VDSVKGRFTI SQDNAKNTLF LQMNSLKPED TAMYYCATDP LWGRKYGGSW SDPSEYNYWG   120
QGTQVTVSS                                                           129

SEQ ID NO: 74        moltype = AA  length = 123
FEATURE              Location/Qualifiers
REGION               1..123
                     note = SLN0044
source               1..123
                     mol_type = protein
                     organism = synthetic construct
SEQUENCE: 74
DVQLVESGGG SVQAGGSLRL SCAASIYTYS TACMAWFRQA PGKEREGVAA IARYGDTTYT    60
DSVKGRFTIS RDVAKNILYL QMSSLKPEDT AMYYCASKSP NSGCDEYAHY ETFGQGTQVT   120
VSS                                                                 123

SEQ ID NO: 75        moltype = AA  length = 125
FEATURE              Location/Qualifiers
REGION               1..125
                     note = SLN0045
source               1..125
                     mol_type = protein
                     organism = synthetic construct
SEQUENCE: 75
EVQLVESGGG SVQAGGSLRL SCTASGYTYS RACMAWFRQA AGKQREWVSW IIADGSTGYA    60
DSVKGRFTIS RDNAKNTLYL DMTSLKPEDT AMYYCAAAYN GGDRCYTLIG LYNHWGQGTQ   120
VTVSS                                                               125

SEQ ID NO: 76        moltype = AA  length = 124
FEATURE              Location/Qualifiers
REGION               1..124
                     note = SLN0049
source               1..124
                     mol_type = protein
                     organism = synthetic construct
SEQUENCE: 76
EVQLVESGGG SVQAGGSLRL SCAASRATNS RYSMGWFRQA PGKEREGVAA IDSIGRTSYA    60
DSVKGRFTIS QDGAKNTLYL QMNSLKPEDT AMYYCAATAW RDWATLREYE YGYWGQGTQV   120
TVSS                                                                124

SEQ ID NO: 77        moltype = AA  length = 128
FEATURE              Location/Qualifiers
REGION               1..128
                     note = SLN0056
source               1..128
                     mol_type = protein
                     organism = synthetic construct
SEQUENCE: 77
```

```
EVQLVESGGG SVQAGGSLRL SCRASGHAYG GNYMGWFRQA PGKEREGVAV LYTGGGSTYY   60
ADSVKGRFTI SEDNAKNTVY LQMDSLKLED TAMYYCALAL GSARWYTSSL DARAYNIWGQ  120
GTQVTVSS                                                          128

SEQ ID NO: 78           moltype = AA   length = 124
FEATURE                 Location/Qualifiers
REGION                  1..124
                        note = SLN0057
source                  1..124
                        mol_type = protein
                        organism = synthetic construct
SEQUENCE: 78
HVQLVESGGG SVQAGGSLRL SCAASGHTYS IYYMAWFRQA PGKEREGVAV IYRGGSTTYA   60
DSAKGRFTVS QDNGKNTVYL QMNSLKAEDT AMYYCAAAHV LHVSSLLPGG YPYWGQGTLV  120
TVSS                                                              124

SEQ ID NO: 79           moltype = AA   length = 123
FEATURE                 Location/Qualifiers
REGION                  1..123
                        note = SLN0059
source                  1..123
                        mol_type = protein
                        organism = synthetic construct
SEQUENCE: 79
HVQLVESGGG SVQSGGSLRL SCAASGITIS NYYMTWFRQA PGKEREGVAG LTRADVTLYA   60
DSVKGRFTIS RDNAKNTLYL QMNSLKPEDT AMYYCAAADR FRVGLREADF SAWGQGTQVT  120
VSS                                                               123

SEQ ID NO: 80           moltype = AA   length = 125
FEATURE                 Location/Qualifiers
REGION                  1..125
                        note = SLN0062
source                  1..125
                        mol_type = protein
                        organism = synthetic construct
SEQUENCE: 80
QVQLVESGGG SVQSGGSLRL SCAASGYTFS RNCMGWFRQT PGKERERVAT VYPGGGSTYY   60
ADSVKGRFTF SQDNAKNAIY LQMNTLKPED TGMYYCAASR RIWSCGSGAG SYDYWGQGTQ  120
VTVSS                                                             125

SEQ ID NO: 81           moltype = AA   length = 128
FEATURE                 Location/Qualifiers
REGION                  1..128
                        note = SLN0064
source                  1..128
                        mol_type = protein
                        organism = synthetic construct
SEQUENCE: 81
HVQLVESGGG SVQAGGSLRL SCAASGYSVS WFCMGWFRQA PGLEREGVAV IDVDSIARYG   60
DSVKGRFTIS QGNSKDTVYL QMNGLKPEDT AMYYCAAKTE RQCRWNWMDW RTYDYPHWGQ  120
GTQVTVSS                                                          128

SEQ ID NO: 82           moltype = AA   length = 123
FEATURE                 Location/Qualifiers
REGION                  1..123
                        note = SLN0065
source                  1..123
                        mol_type = protein
                        organism = synthetic construct
SEQUENCE: 82
EVQLVESGGG SVQAGGSLRL SCLYTDSLFW MGWFRQTPGN EREGVAVTGR DGSTIYADSV   60
QGRFTISRDN AKNTLYLQMN SLKPDDTAMY YCAADQTRYS SLRLLAPNRS ASWGQGTQVT  120
VSS                                                               123

SEQ ID NO: 83           moltype = AA   length = 127
FEATURE                 Location/Qualifiers
REGION                  1..127
                        note = SLN0071
source                  1..127
                        mol_type = protein
                        organism = synthetic construct
SEQUENCE: 83
EVQLVESGGG SVQAGGSLRL SCAGSEYTYS RCCMGWFRQA PGKEREGVVS INVLGGTSYA   60
DSVKGRFTIS RDNAENTLYL QMNSLKPEDT AMYYCAAGLA SAPWRPCGTT TEEYKYWGQG  120
TQVTVSS                                                           127

SEQ ID NO: 84           moltype = AA   length = 127
FEATURE                 Location/Qualifiers
REGION                  1..127
```

```
                        note = SLN0072
source                  1..127
                        mol_type = protein
                        organism = synthetic construct
SEQUENCE: 84
EVQLVESGGG SVQAGGSLRL SCVASGYTGS SSYMGWFRQV PGKEREGVAQ INSRSGSTYY   60
ADSVKGRFTI SQDNAKNTVY LQMTSLKPED TGMYYCAERF GPTFYPVPLG SNLYNYWGQG  120
TQVTVSS                                                            127

SEQ ID NO: 85           moltype = AA   length = 125
FEATURE                 Location/Qualifiers
REGION                  1..125
                        note = SLN0046
source                  1..125
                        mol_type = protein
                        organism = synthetic construct
SEQUENCE: 85
DVQLVESGGG SVQAGGSLRL SCTASGYTYS RACMAWFRQA AGKQREWVSW IIADGSTGYA   60
DSVKGRFTIS RDNAKNTLYL DMTSLKPEDT AMYYCAAAYN GGDRCYTLIG LYNHWGQGTQ  120
VTVSS                                                              125

SEQ ID NO: 86           moltype = AA   length = 127
FEATURE                 Location/Qualifiers
REGION                  1..127
                        note = SLN0058
source                  1..127
                        mol_type = protein
                        organism = synthetic construct
SEQUENCE: 86
HVQLVESGGG SVQAGGSLRL SCTASGYMYT SDCMGWFRQA PGKEREGVAT IATAGGSTGY   60
ADSVKGRFTI SQDNAKNTMY LQMNNLKPED TAMYYCAAWG GAWWYPWCEF VFSNGYWGQG  120
TLVTVSS                                                            127

SEQ ID NO: 87           moltype = AA   length = 126
FEATURE                 Location/Qualifiers
REGION                  1..126
                        note = SLN9008
source                  1..126
                        mol_type = protein
                        organism = synthetic construct
SEQUENCE: 87
DVQLVESGGG SVQAGGSLRL SCQASGYTGG GHCMAWFRQA PGKDREGIAA IYTGTGSTYY   60
ADESVKGRFI ISQDNARSTV YLQMDSLKPE DTGMYYCAAT LLYGCGAWSP RLFGYWGQGT  120
QVTVSS                                                             126

SEQ ID NO: 88           moltype = AA   length = 128
FEATURE                 Location/Qualifiers
REGION                  1..128
                        note = SLN9013
source                  1..128
                        mol_type = protein
                        organism = synthetic construct
SEQUENCE: 88
QVQLVESGGG SVQAGGSLRL SCAASGYTYS RGCMGWFRQA PGKEREGVAS FLHGAASADY   60
ADSVKGRFTI SQDNAKNTMY LQMNNLKPED TAMYYCAANP VVASCHYRLR SKYAYNYWGE  120
GTQVTVSS                                                           128

SEQ ID NO: 89           moltype = AA   length = 128
FEATURE                 Location/Qualifiers
REGION                  1..128
                        note = SLN9015
source                  1..128
                        mol_type = protein
                        organism = synthetic construct
SEQUENCE: 89
DVQLVESGGG SVQAGGSLRL SCRASGHAYS GNYMGWFRQA PGKEREGVAV LYTGGGSTYY   60
ADSVKGRFTI SEDNAKNTVY LQMDSLKLED TAMYYCALVL GSARWYTSSL DARAYNIWGQ  120
GTQVTVSS                                                           128

SEQ ID NO: 90           moltype = AA   length = 123
FEATURE                 Location/Qualifiers
REGION                  1..123
                        note = SLN9025
source                  1..123
                        mol_type = protein
                        organism = synthetic construct
SEQUENCE: 90
HVQLVESGGG SVQAGGSLNV SCAASGYTFN QHCMGWFRQA PGKQREGFLY TYVSFNVTHY   60
ADSVKGRFTI SHDSAENAMY LQMNSLGPED SGMYYCAAGY YSCGVSTTGY NYWGQGTQVT  120
```

```
VSS                                                                              123

SEQ ID NO: 91            moltype = AA   length = 130
FEATURE                  Location/Qualifiers
REGION                   1..130
                         note = SLN9026
source                   1..130
                         mol_type = protein
                         organism = synthetic construct
SEQUENCE: 91
HVQLVESGGG SVQAGGSLRL SCAASGDTYS SKCMAWFRQV PGKEREGVAA IDTSRGRAYL      60
TDSVKGRFTI SQDNAKNTVY LQMNSLKPED TAMYYCAASN TFYNCGALNL GIGAGLVAYW     120
GQGTQVTVSS                                                           130

SEQ ID NO: 92            moltype = AA   length = 129
FEATURE                  Location/Qualifiers
REGION                   1..129
                         note = 1902-2-1-mm-F7
source                   1..129
                         mol_type = protein
                         organism = synthetic construct
SEQUENCE: 92
HVQLVESGGG SVQTGGSLRL SCAASGYTIS RACMGWFRQA PGKEREMVAR VYSDGSQSYY      60
PDSVKGRFTI SQDNAKNTVY LQMDRLEPED TAIYYCAALL MSDYYSCRVR FHQSDFRDWG     120
QGTQVTVSS                                                            129

SEQ ID NO: 93            moltype = AA   length = 128
FEATURE                  Location/Qualifiers
REGION                   1..128
                         note = 1902-2-1-hh-B12
source                   1..128
                         mol_type = protein
                         organism = synthetic construct
SEQUENCE: 93
EVQLVESGGG SVQAGGSLRL SCVASGYTFG KYCMGWIRQV PGKEREGVAA IDSDGTTRYA      60
DSVQGRFTIS QDNAKNTLVL EMNSLKLEDS AMYYCAADRW SMKYYSDYAL FPGGYNYWGQ     120
GTLVTVSS                                                             128

SEQ ID NO: 94            moltype = AA   length = 130
FEATURE                  Location/Qualifiers
REGION                   1..130
                         note = 1902-2-1-hm-D12
source                   1..130
                         mol_type = protein
                         organism = synthetic construct
SEQUENCE: 94
DVQLVESGGG SVQAGESLRL SCGASGYTYR NYCMAWFRLA PGKEREGVAN MNSYDWTDYD      60
DSVKGRFTIS QDNAANTWYL QMNSLKPEDT AMYYCALRDC ALRYCTRSYC TREAHFFKYW     120
GQGTQVTVSS                                                           130

SEQ ID NO: 95            moltype = AA   length = 128
FEATURE                  Location/Qualifiers
REGION                   1..128
                         note = SLN0097
source                   1..128
                         mol_type = protein
                         organism = synthetic construct
SEQUENCE: 95
EVQLVESGGG LVQPGGSLRL SCAASGHAYG GNYMGWFRQA PGKGLEGVSV LYTGGGSTYY      60
ADSVKGRFTI SRDNSKNTLY LQMNSLRAED TAVYYCALAL GSARWYTSSL DARAYNIWGQ     120
GTLVTVSS                                                             128

SEQ ID NO: 96            moltype = AA   length = 128
FEATURE                  Location/Qualifiers
REGION                   1..128
                         note = SLN9079
source                   1..128
                         mol_type = protein
                         organism = synthetic construct
SEQUENCE: 96
EVQLVESGGG LVQPGGSLRL SCAASGHAYG GNYMGWFRQA PGKGLEGVAV LYTGGGSTYY      60
ADSVKGRFTI SEDNSKNTLY LQMNSLRAED TAVYYCALAL GSARWYTSSL DARAYNIWGQ     120
GTLVTVSS                                                             128

SEQ ID NO: 97            moltype = AA   length = 127
FEATURE                  Location/Qualifiers
REGION                   1..127
                         note = SLN9060
source                   1..127
```

```
                          mol_type = protein
                          organism = synthetic construct
SEQUENCE: 97
EVQLVESGGG LVQPGGSLRL SCAASGYTGS SSYMGWFRQA PGKGLEGVSQ IQSRSGSTYY    60
ADSVKGRFTI SRDNSKNTLY LQMNSLRAED TAVYYCAERF GPTFYPVPLG SNLYNYWGQG   120
TLVTVSS                                                             127

SEQ ID NO: 98             moltype = AA  length = 127
FEATURE                   Location/Qualifiers
REGION                    1..127
                          note = SLN9061
source                    1..127
                          mol_type = protein
                          organism = synthetic construct
SEQUENCE: 98
EVQLVESGGG LVQPGGSLRL SCAASGYTGS SSYMGWFRQA PGKGLEGVSQ INARSGSTYY    60
ADSVKGRFTI SRDNSKNTLY LQMNSLRAED TAVYYCAERF GPTFYPVPLG SNLYNYWGQG   120
TLVTVSS                                                             127

SEQ ID NO: 99             moltype = AA  length = 127
FEATURE                   Location/Qualifiers
REGION                    1..127
                          note = SLN9062
source                    1..127
                          mol_type = protein
                          organism = synthetic construct
SEQUENCE: 99
EVQLVESGGG LVQPGGSLRL SCAASGYTGS SSYMGWFRQA PGKGLEGVCQ INSRSGSTYY    60
ADSVKGRFTC SRDNSKNTLY LQMNSLRAED TAVYYCAERF GPTFYPVPLG SNLYNYWGQG   120
TLVTVSS                                                             127

SEQ ID NO: 100            moltype = AA  length = 127
FEATURE                   Location/Qualifiers
REGION                    1..127
                          note = SLN9077
source                    1..127
                          mol_type = protein
                          organism = synthetic construct
SEQUENCE: 100
EVQLVESGGG LVQPGGSLRL SCAASGYTGS SSYMGWFRQA PGKGLEGVSQ INSRSGSTYY    60
ADSVKGRFTI SRDNSKNTLY LQMNSLRAED TAVYYCAERF GPTFYTGNLG SNLYNYWGQG   120
TLVTVSS                                                             127

SEQ ID NO: 101            moltype = AA  length = 127
FEATURE                   Location/Qualifiers
REGION                    1..127
                          note = SLN9058
source                    1..127
                          mol_type = protein
                          organism = synthetic construct
SEQUENCE: 101
EVQLVESGGG LVQPGGSLRL SCAASGYTGS SSYMGWFRQA PGKGREGVSQ INSRSGSTYY    60
ADSVKGRFTI SRDNSKNTLY LQMNSLRAED TAVYYCAERF GPTFYPVPLG SNLYNYWGQG   120
TLVTVSS                                                             127

SEQ ID NO: 102            moltype = AA  length = 128
FEATURE                   Location/Qualifiers
REGION                    1..128
                          note = SLN0104
source                    1..128
                          mol_type = protein
                          organism = synthetic construct
SEQUENCE: 102
EVQLVESGGG LVQPGGSLRL SCAASGHAYG GNYMGWFRQA PGKGLEGVAV LYTGGGSTYY    60
ADSVKGRFTI SRDNAKNSLY LQMNSLRAED TAVYYCALAL GSARWYTSSL DARAYNIWGQ   120
GTLVTVSS                                                            128

SEQ ID NO: 103            moltype = AA  length = 128
FEATURE                   Location/Qualifiers
REGION                    1..128
                          note = SLN0100
source                    1..128
                          mol_type = protein
                          organism = synthetic construct
SEQUENCE: 103
EVQLVESGGG LVQPGGSLRL SCAASGHAYG GNYMGWFRQA PGKGLEGVSV LYTGGGSTYY    60
ADSVKGRFTI SRDNAKNSLY LQMNSLRAED TAVYYCALAL GSARWYTSSL DARAYNIWGQ   120
GTLVTVSS                                                            128
```

| | | |
|---|---|---|
| SEQ ID NO: 104 | moltype = AA   length = 127 | |
| FEATURE | Location/Qualifiers | |
| REGION | 1..127 | |
| | note = SLN0105 | |
| source | 1..127 | |
| | mol_type = protein | |
| | organism = synthetic construct | |
| SEQUENCE: 104 | | |
| EVQLVESGGG LVQPGGSLRL SCAASGYTGS SSYMGWFRQA PGKGLEGVSQ INSRSGSTYY | | 60 |
| ADSVKGRFTI SRDNSKNTLY LQMNSLRAED TAVYYCAERF GPTFYPVPLG SNLYNYWGQG | | 120 |
| TLVTVSS | | 127 |
| | | |
| SEQ ID NO: 105 | moltype = AA   length = 174 | |
| FEATURE | Location/Qualifiers | |
| REGION | 1..174 | |
| | note = GLP-1-9056 | |
| source | 1..174 | |
| | mol_type = protein | |
| | organism = synthetic construct | |
| SEQUENCE: 105 | | |
| HGEGTFTSDV SSYLEEQAAK EFIAWLVKGG GGGGSGGGG SGGGGSEVQL VESGGGLVQP | | 60 |
| GGSLRLSCAA SGHAYGGNYM GWFRQAPGKG LEGVAVLYTG GSTYYADSV KGRFTISEDN | | 120 |
| SKNTVYLQMN SLRAEDTAVY YCALALGSAR WYTSSLDARA YNIWGQGTLV TVSS | | 174 |
| | | |
| SEQ ID NO: 106 | moltype = AA   length = 506 | |
| FEATURE | Location/Qualifiers | |
| REGION | 1..506 | |
| | note = 0072-PE38 | |
| source | 1..506 | |
| | mol_type = protein | |
| | organism = synthetic construct | |
| SEQUENCE: 106 | | |
| EVQLVESGGG SVQAGGSLRL SCVASGYTGS SSYMGWFRQV PGKEREGVAQ INSRSGSTYY | | 60 |
| ADSVKGRFTI SQDNAKNTVY LQMTSLKPED TGMYYCAERF GPTFYPVPLG SNLYNYWGQG | | 120 |
| TQVTVSSEFP KPSTPPGSSG GAPPEGGSLA ALTAHQACHL PLETFTRHRQ PRGWEQLEQC | | 180 |
| GYPVQRLVAL YLAARLSWNQ VDQVIRNALA SPGSGGDLGE AIREQPEQAR LALTLAAAES | | 240 |
| ERFVRQGTGN DEAGAANADV VSLTCPVAAG ECAGPADSGD ALLERNYPTG AEFLGDGGDV | | 300 |
| SFSTRGTQNW TVERLLQAHR QLEERGYVFV GYHGTFLEAA QSIVFGGVRA RSQDLDAIWR | | 360 |
| GFYIAGDPAL AYGYAQDQEP DARGRIRNGA LLRVYVPRSS LPGFYRTSLT LAAPEAAGEV | | 420 |
| ERLIGHPLPL RLDAITGPEE EGGRLETILG WPLAERTVVI PSAIPTDPRN VGGDLDPSSI | | 480 |
| PDKEQAISAL PDYASQPGKP PREDLK | | 506 |
| | | |
| SEQ ID NO: 107 | moltype = AA   length = 385 | |
| FEATURE | Location/Qualifiers | |
| REGION | 1..385 | |
| | note = SLN0041(OVA) | |
| source | 1..385 | |
| | mol_type = protein | |
| | organism = synthetic construct | |
| SEQUENCE: 107 | | |
| GSIGAASMEF CFDVFKELKV HHANENIFYC PIAIMSALAM VYLGAKDSTR TQINKVVRFD | | 60 |
| KLPGFGDSIE AQCGTSVNVH SSLRDILNQI TKPNDVYSFS LASRLYAEER YPILPEYLQC | | 120 |
| VKELYRGGLE PINFQTAADQ ARELINSWVE SQTNGIIRNV LQPSSVDSQT AMVLVNAIVF | | 180 |
| KGLWEKAFKD EDTQAMPFRV TEQESKPVQM MYQIGLFRVA SMASEKMKIL ELPFASGTMS | | 240 |
| MLVLLPDEVS GLEQLESIIN FEKLTEWTSS NVMEERKIKV YLPRMKMEEK YNLTSVLMAM | | 300 |
| GITDVFSSSA NLSGISSAES LKISQAVHAA HAEINEAGRE VVGSAEAGVD AASVSEEFRA | | 360 |
| DHPFLFCIKH IATNAVLFFG RCVSP | | 385 |
| | | |
| SEQ ID NO: 108 | moltype = AA   length = 28 | |
| FEATURE | Location/Qualifiers | |
| REGION | 1..28 | |
| | note = GLP-1 | |
| source | 1..28 | |
| | mol_type = protein | |
| | organism = synthetic construct | |
| SEQUENCE: 108 | | |
| HGEGTFTSDV SSYLEEQAAK EFIAWLVK | | 28 |
| | | |
| SEQ ID NO: 109 | moltype = AA   length = 219 | |
| FEATURE | Location/Qualifiers | |
| REGION | 1..219 | |
| | note = PE-38 | |
| source | 1..219 | |
| | mol_type = protein | |
| | organism = synthetic construct | |
| SEQUENCE: 109 | | |
| PTGAEFLGDG GDVSFSTRGT QNWTVERLLQ AHRQLEERGY VFVGYHGTFL EAAQSIVFGG | | 60 |
| VRARSQDLDA IWRGFYIAGD PALAYGYAQD QEPDARGRIR NGALLRVYVP RSSLPGFYRT | | 120 |
| SLTLAAPEAA GEVERLIGHP LPLRLDAITG PEEEGGRLET ILGWPLAERT VVIPSAIPTD | | 180 |

```
PRNVGGDLDP SSIPDKEQAI SALPDYASQP GKPPREDLK                          219

SEQ ID NO: 110          moltype = AA  length = 129
FEATURE                 Location/Qualifiers
REGION                  1..129
                        note = SLN0066
source                  1..129
                        mol_type = protein
                        organism = synthetic construct
SEQUENCE: 110
HVQLVESGGG SVQAGGSLRL SCVASGIGHG FNNNCMGWFR QAPGKEREGV AAVYTGGGTP    60
YYADSVKGRF TLSQDNAKNT LYLQMNGLDP EDTAMYYCVA DIWRTYRCGA GDTTVFDYRG   120
QGTLVTVSS                                                          129
```

What is claimed is:

1. A transferrin-binding protein, comprising:
a VHH or a transferrin-binding fragment thereof,
wherein VHH comprises CDR1, CDR2 and CDR3,
wherein the CDR1 comprises the amino acid sequence of SEQ ID NO: 1,
wherein the CDR2 comprises the amino acid sequence of SEQ ID NO: 22, and
wherein the CDR3 comprises the amino acid sequence of SEQ ID NO: 45.

2. The transferrin-binding protein of claim 1 that comprises the amino acid sequence of SEQ ID NO: 70, 77, 95, 96, 102 and 103.

3. The transferrin-binding protein of claim 1, wherein said transferrin-binding protein is a single domain antibody comprising the CDRs of SEQ ID NOS: 1, 22 and 45.

4. The transferrin-binding protein of claim 1 that comprises a heavy chain variable region VH and said heavy chain variable region VH comprises an amino acid sequence as set forth in any one of SEQ ID NOs: 70, 77, 95, 96, 102 and 103.

5. A polypeptide, comprising the transferrin-binding protein of claim 1, and a therapeutic agent.

6. The polypeptide of claim 5, wherein said therapeutic agent is an engineered cytotoxic *Pseudomonas* exotoxin A (PE38), or a glucagon-like peptide-1 (GLP-1).

7. The polypeptide of claim 5, wherein said therapeutic agent and said antigen-binding protein are directly or indirectly linked.

8. A pharmaceutical composition, comprising the transferrin-binding protein of claim 1.

9. The transferrin-binding protein of claim 1, wherein said transferrin-binding protein comprises VHH.

10. An isolated nucleic acid molecule, encoding the transferrin-binding protein of claim 1.

11. A vector, comprising the nucleic acid molecule of claim 10.

12. A cell, comprising the nucleic acid molecule of claim 10.

13. A method of preparing a transferrin-binding protein, comprising culturing the cell of claim 12 under conditions that allow said transferrin-binding protein to be expressed.

* * * * *